United States Patent
Yamamoto et al.

(10) Patent No.: US 10,180,525 B2
(45) Date of Patent: Jan. 15, 2019

(54) OPTICAL PLATE, LIGHT IRRADIATION DEVICE, LIGHT MEASUREMENT DEVICE, LIGHT IRRADIATION METHOD, AND LIGHT MEASUREMENT METHOD

(71) Applicant: HAMAMATSU PHOTONICS K.K., Hamamatsu-shi, Shizuoka (JP)

(72) Inventors: Satoshi Yamamoto, Hamamatsu (JP); Kenshi Fukumitsu, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 15/313,195

(22) PCT Filed: May 15, 2015

(86) PCT No.: PCT/JP2015/064097
§ 371 (c)(1),
(2) Date: Nov. 22, 2016

(87) PCT Pub. No.: WO2015/182412
PCT Pub. Date: Dec. 3, 2015

(65) Prior Publication Data
US 2017/0146720 A1 May 25, 2017

(30) Foreign Application Priority Data
May 26, 2014 (JP) .................. 2014-108043

(51) Int. Cl.
*F21V 8/00* (2006.01)
*F21S 2/00* (2016.01)
(Continued)

(52) U.S. Cl.
CPC .......... *G02B 6/0035* (2013.01); *A61B 5/1455* (2013.01); *B23K 26/0057* (2013.01);
(Continued)

(58) Field of Classification Search
CPC .. G01N 33/574; G01N 33/5011; G01N 21/64; G01N 21/6458; G01N 2500/04;
(Continued)

(56) References Cited

U.S. PATENT DOCUMENTS 5,899,552 A 5/1999 Yokoyama et al.
2003/0120137 A1 6/2003 Pawluczyk
(Continued)

FOREIGN PATENT DOCUMENTS

CN 102365544 2/2012
JP H11-023243 1/1999
(Continued)

OTHER PUBLICATIONS

International Preliminary Report on Patentability dated Dec. 8, 2016 for PCT/JP2015/064097.

*Primary Examiner* — Michael P Stafira
(74) *Attorney, Agent, or Firm* — Drinker Biddle & Reath LLP

(57) ABSTRACT

An optical plate is an optical plate for irradiating a target with light, and includes a light input surface for inputting the light, a light output surface for outputting the light, a back surface opposite to the light output surface, and a light diffusion portion formed at least inside the optical plate by converging laser light, for diffusing the light. The light input surface is a surface between the light output surface and the back surface, and the light input from the light input surface is diffused in the light diffusion portion and output from the light output surface.

9 Claims, 24 Drawing Sheets

(51) Int. Cl.
| | |
|---|---|
| *G01N 21/01* | (2006.01) |
| *G01N 21/03* | (2006.01) |
| *G01N 21/27* | (2006.01) |
| *G01N 21/64* | (2006.01) |
| *G02B 6/00* | (2006.01) |
| *B23K 26/53* | (2014.01) |
| *B23K 26/00* | (2014.01) |
| *B23K 26/03* | (2006.01) |
| *G01N 21/47* | (2006.01) |
| *G01N 21/55* | (2014.01) |
| *G01N 33/483* | (2006.01) |
| *A61B 5/1455* | (2006.01) |
| *G01N 21/25* | (2006.01) |
| *G01N 21/49* | (2006.01) |

(52) U.S. Cl.
CPC ............ *B23K 26/032* (2013.01); *B23K 26/53* (2015.10); *F21S 2/00* (2013.01); *G01N 21/01* (2013.01); *G01N 21/03* (2013.01); *G01N 21/253* (2013.01); *G01N 21/27* (2013.01); *G01N 21/47* (2013.01); *G01N 21/49* (2013.01); *G01N 21/55* (2013.01); *G01N 21/64* (2013.01); *G01N 21/6428* (2013.01); *G01N 21/6452* (2013.01); *G01N 21/6456* (2013.01); *G01N 33/4833* (2013.01); *G02B 6/00* (2013.01); *G01N 2201/068* (2013.01); *G01N 2201/06113* (2013.01)

(58) Field of Classification Search
CPC .. G01N 2500/20; G01N 27/02; G01N 27/021; G01N 27/3278; G01N 33/4836; G01N 33/5044; G01N 33/54306; G01N 33/54353; G01N 33/54
See application file for complete search history.

(56) References Cited

U.S. PATENT DOCUMENTS

| | | |
|---|---|---|
| 2008/0095669 A1 | 4/2008 | Kang et al. |
| 2010/0184616 A1 | 7/2010 | Hillendahl et al. |
| 2012/0188791 A1 | 7/2012 | Voloschenko et al. |
| 2013/0258076 A1 | 10/2013 | Fujimoto et al. |

FOREIGN PATENT DOCUMENTS

| | | |
|---|---|---|
| JP | 2009-056467 A | 3/2009 |
| JP | 2010-070399 | 4/2010 |
| JP | 2010-230396 A | 10/2010 |
| JP | 2010-230397 A | 10/2010 |
| JP | 2013-171056 A | 9/2013 |
| JP | 2013-228361 A | 11/2013 |
| WO | WO-2005/054826 A1 | 6/2005 |
| WO | WO 2013/069452 | 5/2013 |

Fig.4
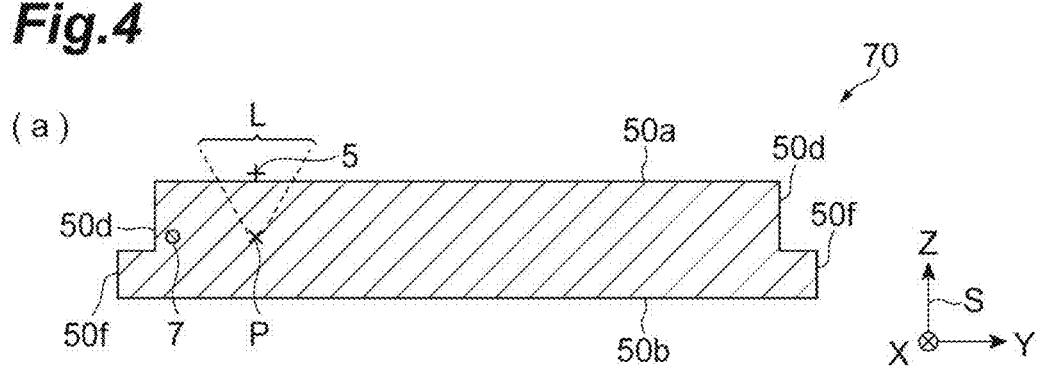
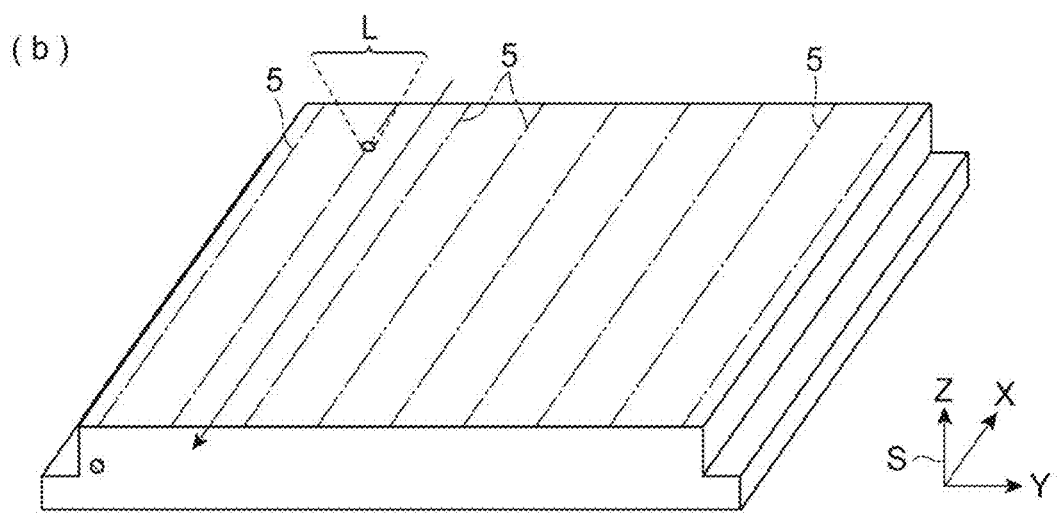
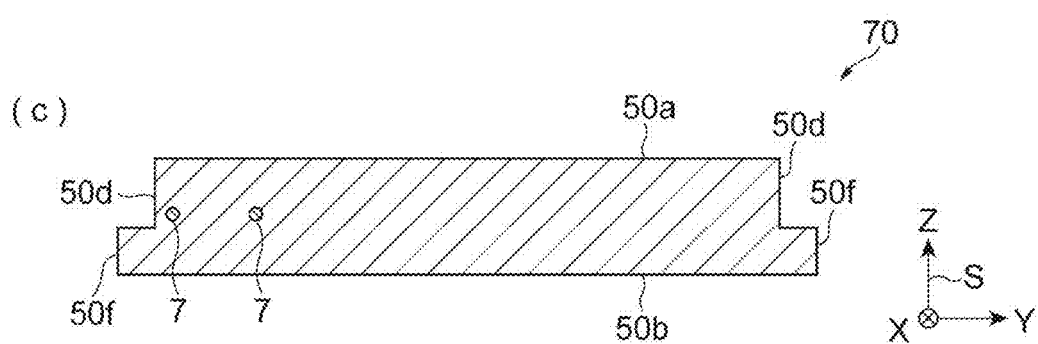

Fig.6
(a)
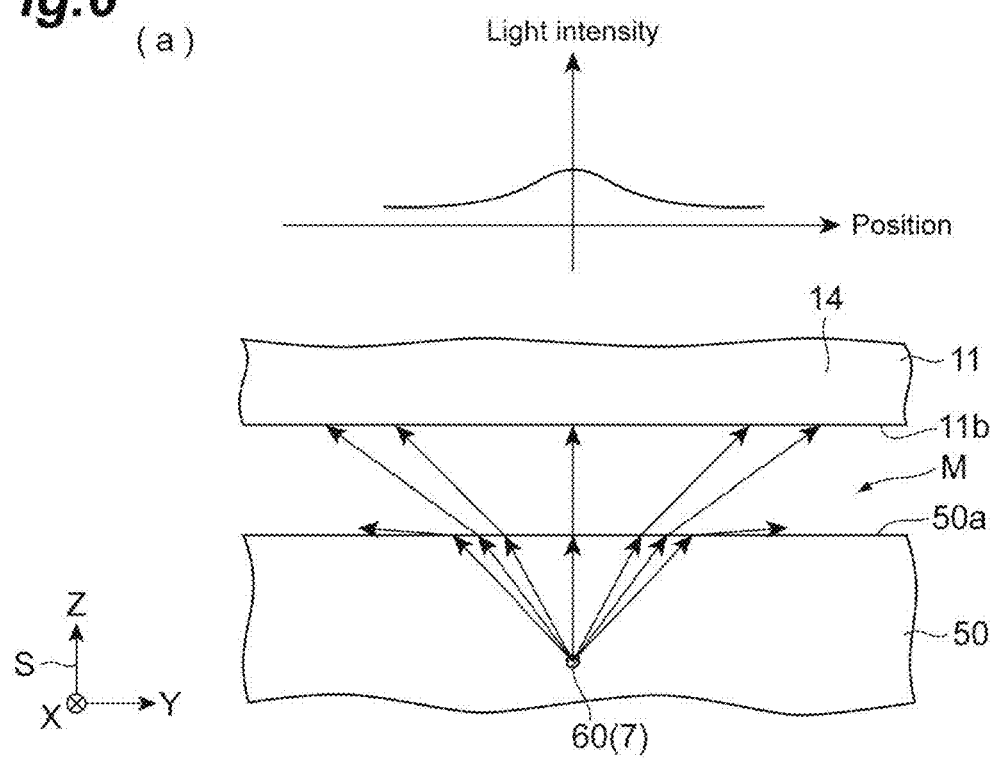
(b)
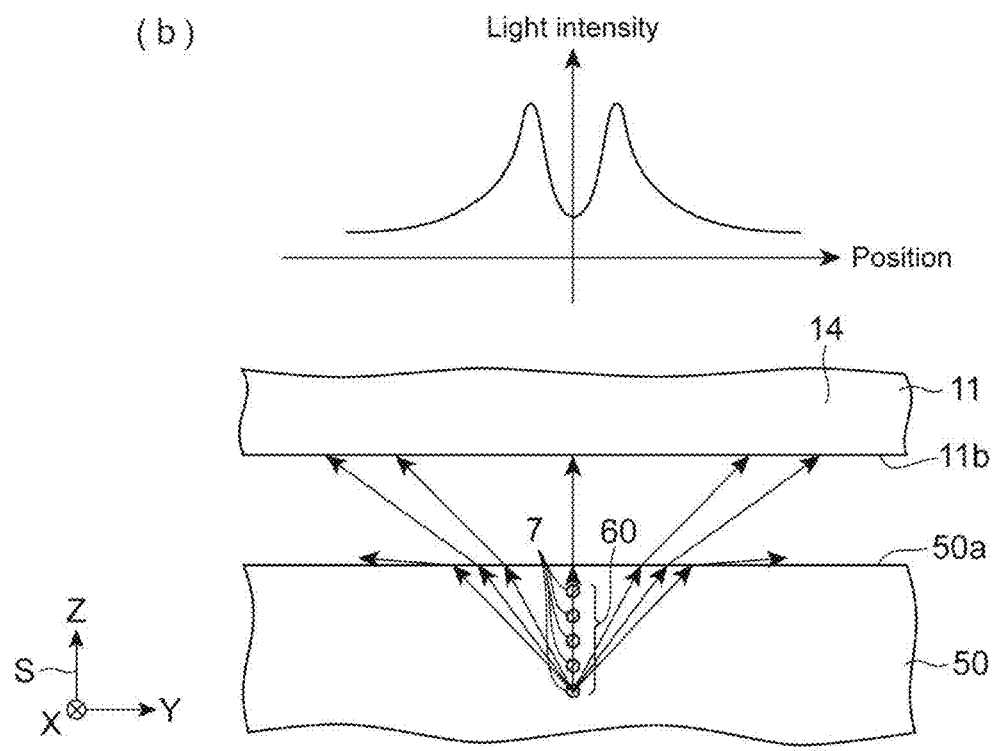

Fig.8
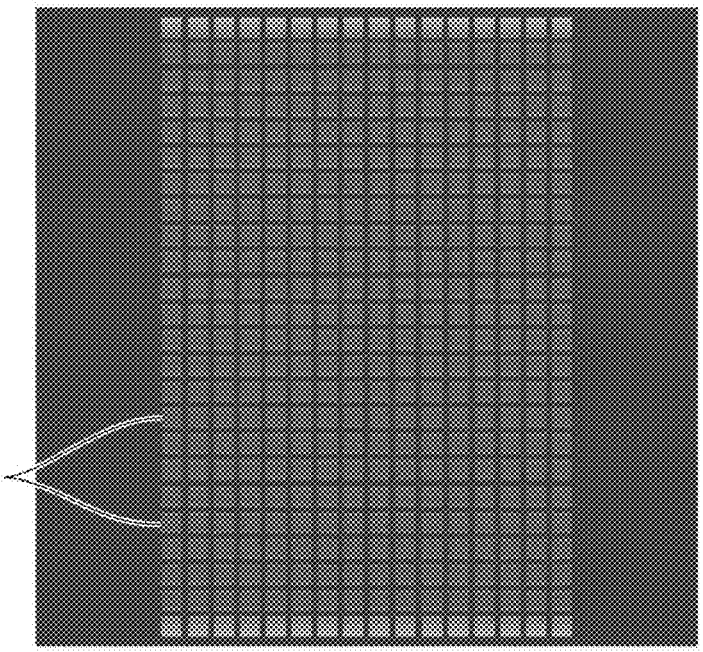
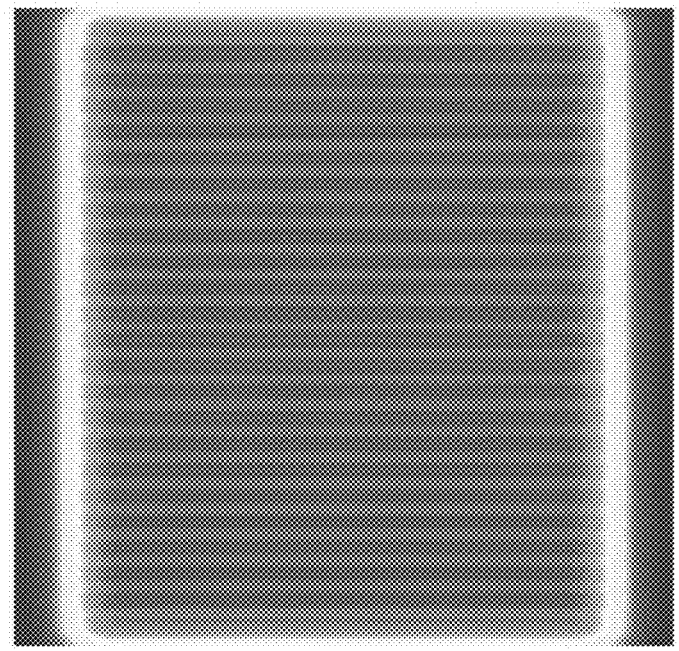

Fig.19
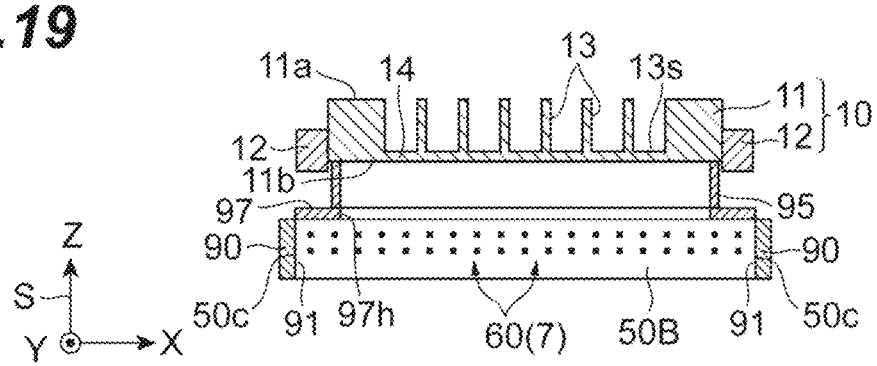
(a)
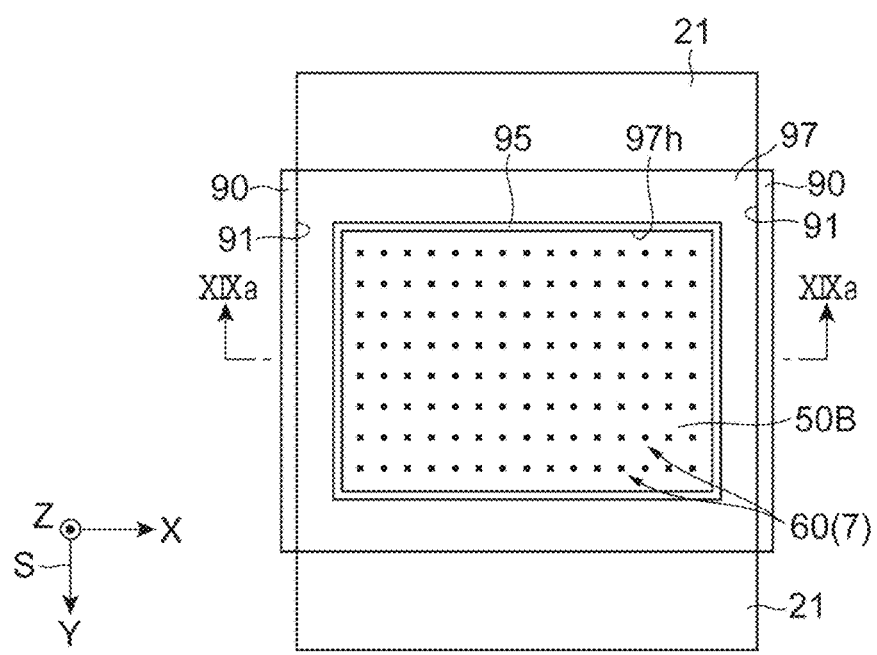
(b)
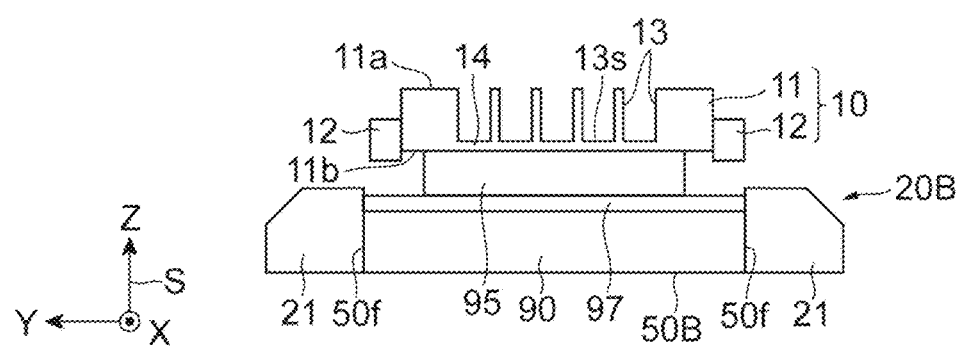
(c)

Fig.20
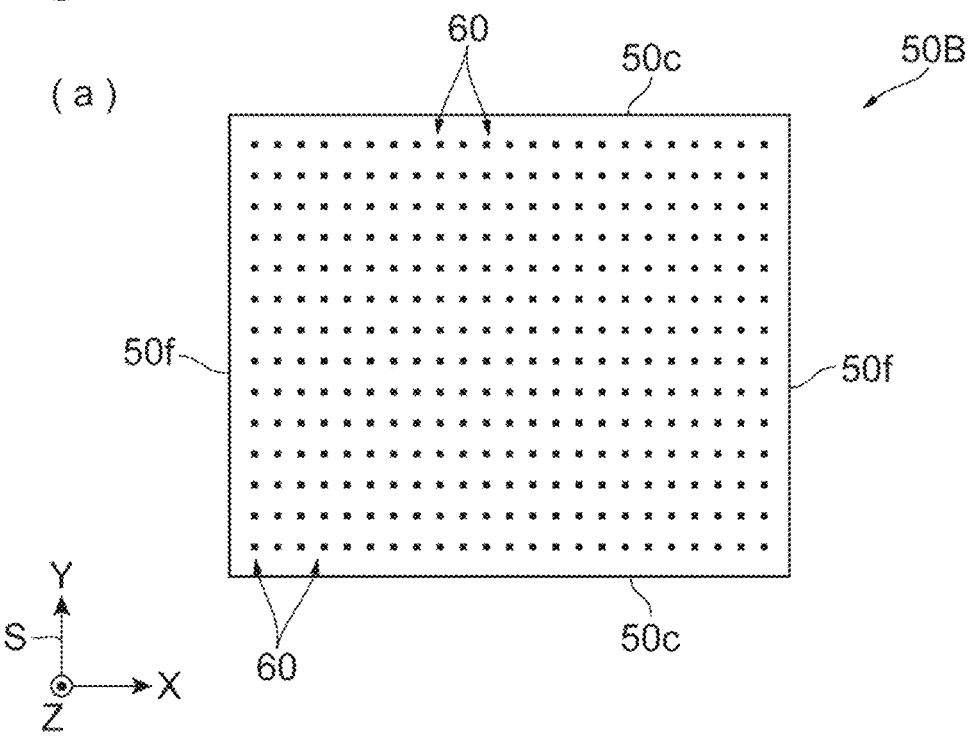
(a)
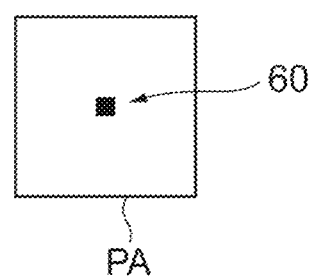
(b)

Fig.22
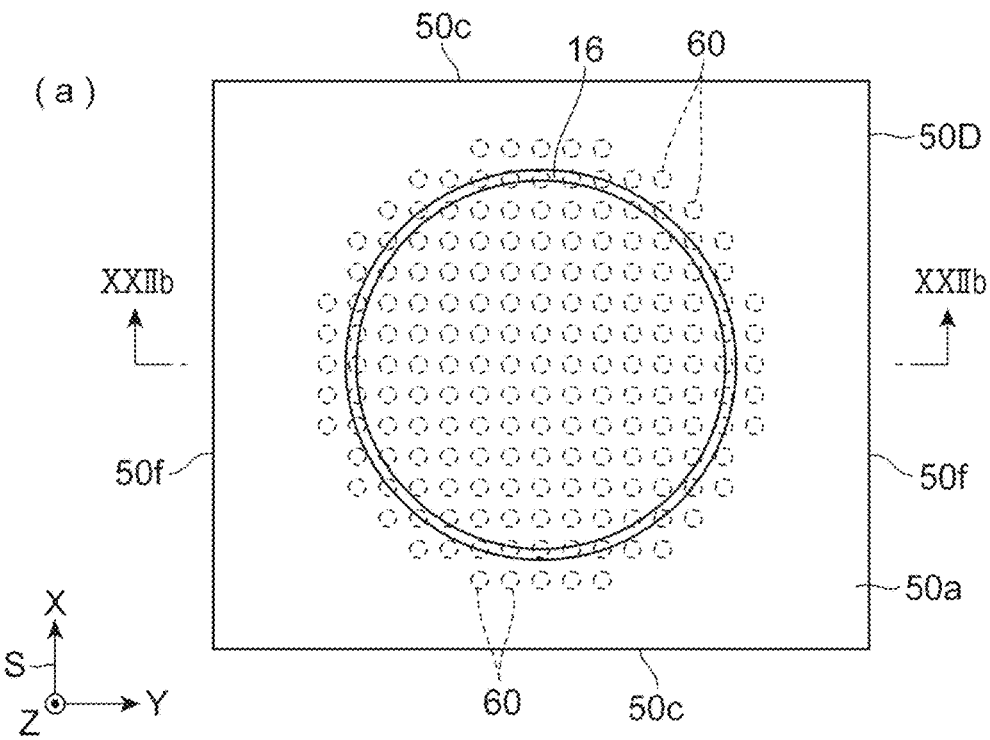
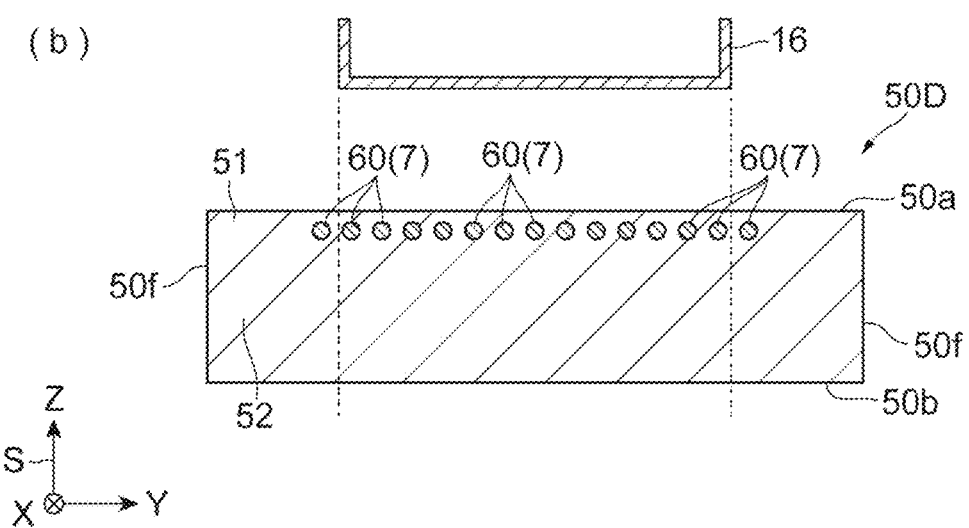

*Fig.24*
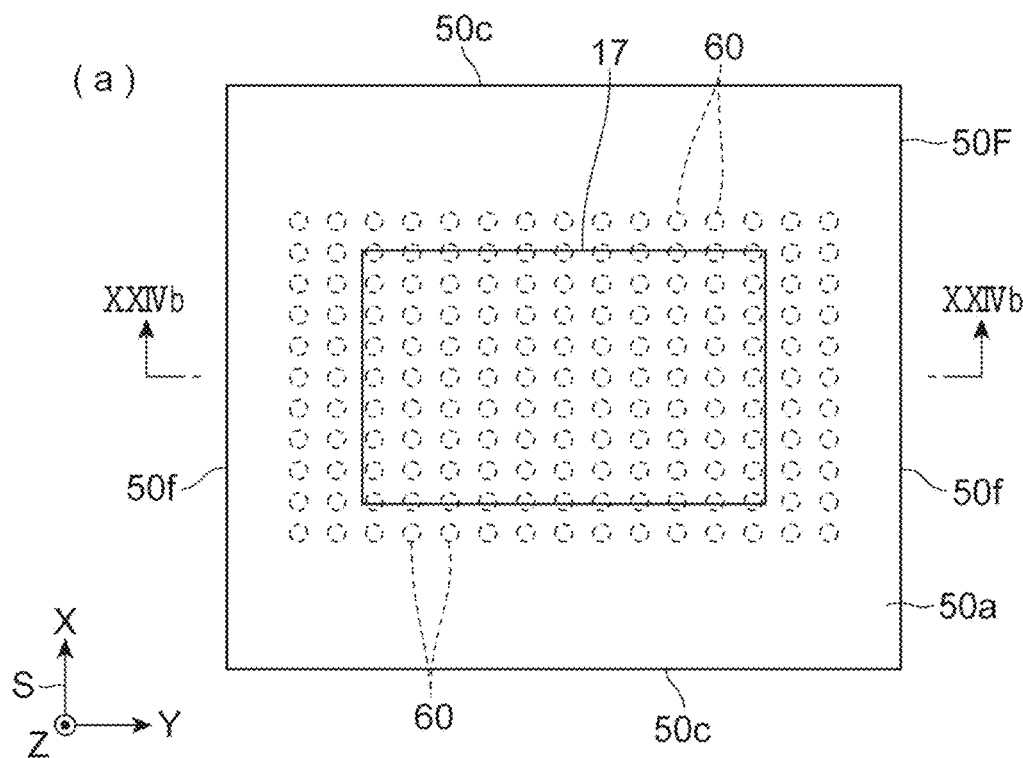
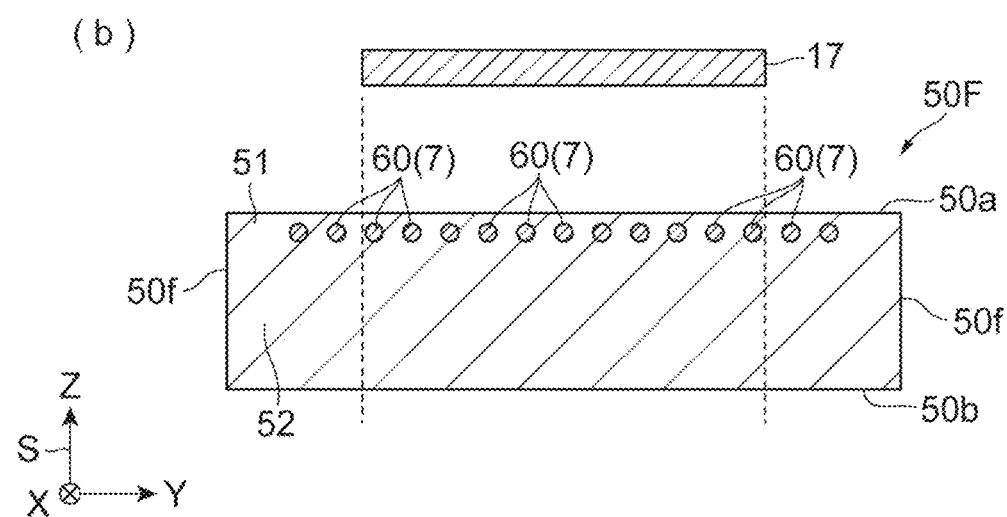

OPTICAL PLATE, LIGHT IRRADIATION DEVICE, LIGHT MEASUREMENT DEVICE, LIGHT IRRADIATION METHOD, AND LIGHT MEASUREMENT METHOD

TECHNICAL FIELD

An aspect of the present invention relates to an optical plate, a light irradiation apparatus, a light measurement system, a light irradiation method, and a light measurement method.

BACKGROUND ART

Patent Literature 1 discloses a light irradiation apparatus that irradiates a micro-plate that holds a measurement target in a plurality of wells with light. This light irradiation apparatus includes a light guide member having a main surface in which a plurality of convex portions are formed, a back surface that is a surface opposite to the main surface, and side surfaces substantially perpendicular to the main surface. Further, this light irradiation apparatus includes a light source that inputs light to the light guide member from the side surface of the light guide member. The light guide member is disposed so that an upper surface of the convex portion is in contact with a back surface of the micro-plate.

CITATION LIST

Patent Literature

[Patent Literature 1] Japanese Unexamined Patent Publication No. 2010-230397

SUMMARY OF INVENTION

Technical Problem

In the light irradiation apparatus described in Patent Literature 1, the light input to the light guide member from the side surface of the light guide member is reflected by a main surface and a back surface of the light guide member, input to the convex portions, and then input to the wells of the macro-plate from the upper surface of the convex portions. In this case, light inclined with respect to a depth direction of the wells is input to the wells of the micro-plate. Therefore, the measurement target can be uniformly irradiated with the light, unlike a case in which the light is input in the depth direction of the wells.

Incidentally, in order to uniformly irradiate the measurement target with the light using the light guide member described above, it is necessary for a shape of the convex portions to be processed according to an arrangement or a shape of the wells holding the measurement target. However, in practice, when the light guide member is formed of quartz or the like, a relatively enhanced processing technology is required for processing for forming the convex portions, and it is difficult for the convex portions to be processed into a desired shape. In other words, it is not easy for the convex portions to be processed so that light is radiated according to desired irradiation conditions.

An aspect of the present invention has been made in view of such circumstances, and an object thereof is to provide an optical plate, a light irradiation apparatus, a light measurement system, a light irradiation method, and a light measurement method capable of allowing irradiation with light according to desired irradiation conditions.

Solution to Problem

In order to solve the above problems, an optical plate according to an aspect of the present invention is an optical plate for irradiating a target with light, including: a light input surface for inputting the light (input light); a light output surface for outputting the light (output light); a back surface opposite to the light output surface; and a light diffusion portion formed at least inside the optical plate by converging laser light, and for diffusing the light, wherein the light input surface is a surface between the light output surface and the back surface, and the light (input light) input from the light input surface is diffused in the light diffusion portion and output from the light output surface.

This optical plate includes the light diffusion portion that diffuses the light input from the light input surface, and outputs the light from the light output surface. That is, the light (input light) input from the light input surface is diffused inside the optical plate in the light diffusion portions, and output from the light output surface as output light. Therefore, if the optical plate is disposed so that the light output surface faces the target, it is possible to irradiate the target with the output light from the light output surface. In particular, in the optical plate, the light diffusion portions are formed by converging the laser light on a member serving as the optical plate (that is, using laser processing). Therefore, it is possible to perform irradiation with light according to desired irradiation conditions, unlike a case in which a convex portion or a concave portion is actually formed in the member.

The optical plate according to an aspect of the present invention may include a light guide portion for guiding the light between the light input surface and a surface facing the light input surface. In this case, light input from the light input surface is diffused by the light diffusion portions and output while being guided between the light input surface and an opposite surface thereto by the light guide portion. Therefore, it is possible to more uniformly irradiate the target present at each place on the region in which the optical plate is disposed, with the light.

The optical plate according to an aspect of the present invention may include a first portion in which the light diffusion portion is formed, and a second portion formed integrally with the first portion, and the light guide portion may be formed in the second portion. In this case, if laser processing is controlled, for example, so that the light diffusion portions are not formed in the second portion among the first and second portions formed integrally with each other, it is possible to form the light guide portion using the second portion. That is, in this case, it is possible to form the light guide portion inside the optical plate by control of laser processing.

In the optical plate according to an aspect of the present invention, the optical plate may be formed by coupling a first portion in which the light diffusion portion is formed to a second portion formed separately from the first portion, and the light guide portion may be formed in the second portion. In this case, if the first portion in which the light diffusion portions are formed using laser processing and the second portion in which, for example, light diffusion portions are not formed are prepared and coupled to each other, the light guide portion can be formed of the second portion.

In the optical plate according to an aspect of the present invention, the light diffusion portion may be formed over at least a portion between the light output surface and the back surface. In this case, it is possible to increase the amount of light that is output from a region adjacent to the light diffusion portion.

In the optical plate according to an aspect of the present invention, the light diffusion portion may be formed of a plurality of light diffusion layers formed by converging laser light. In this case, it is possible to increase the amount of light that is diffused by the light diffusion portions.

The optical plate according to an aspect of the present invention may further include a reflective portion extending in a direction intersecting the light output surface, and for reflecting the light. In this case, it is possible to more uniformly irradiate a target with the light.

A light irradiation apparatus according to an aspect of the present invention includes an optical plate described above, and a light source for outputting light (input light) to be input to the light input surface. Further, a light measurement system according to an aspect of the present invention includes: the light irradiation apparatus described above; a holding member for holding the target; and a light detector for detecting measurement light from the target irradiated with the light (output light) output from the light output surface.

Further, a light irradiation method according to an aspect of the present invention is a method for irradiating a target with light using an optical plate including a light output surface for outputting light (output light), a back surface opposite to the light output surface, a light input surface being a surface between the light output surface and the back surface and for inputting light (input light), and a light diffusion portion formed by converging laser light, the method including: inputting the light (input light) to the light input surface; diffusing the input light in the light diffusion portion; outputting the diffused light (output light) from the light output surface; and irradiating the target with the output light.

Further, a light measurement method according to an aspect of the present invention is a method for irradiating a target with light using an optical plate including a light output surface for outputting light (output light), a back surface opposite to the light output surface, a light input surface being a surface between the light output surface and the back surface, and for inputting light (input light), and a light diffusion portion formed by converging laser light, and detecting measurement light from the target irradiated with the light (output light), the method including: inputting the light (input light) to the light input surface; diffusing the input light in the light diffusion portion; outputting the diffused light (output light) from the light output surface; irradiating the target with the output light; and detecting the measurement light from the target transmitted through the light output surface and the back surface.

The light irradiation apparatus and the light measurement system include the optical plate described above. Further, in the light irradiation method and the light measurement method, the optical plate described above is used. Therefore, for the same reason, it is possible to perform irradiation with light according to desired irradiation conditions.

In the light measurement system according to an aspect of the present invention, the light detector may detect the measurement light transmitted through the optical plate and output from the back surface.

Advantageous Effects of Invention

According to an aspect of the present invention, it is possible to provide the optical plate, the light irradiation apparatus, the light measurement system, the light irradiation method, and the light measurement method capable of allowing irradiation with light according to desired irradiation conditions.

BRIEF DESCRIPTION OF DRAWINGS

FIG. 4 is a diagram illustrating main processes of a method of forming a light diffusion portion.

FIG. 6 is a diagram illustrating a relationship between a configuration of the light diffusion portion and an intensity distribution of light output from the optical plate.

FIG. 8 is a diagram illustrating a simulation result of light intensity when viewed in a third direction.

FIG. 19 is a diagram illustrating a configuration of a light measurement system according to a third embodiment.

FIG. 20 is a diagram illustrating a configuration of the optical plate illustrated in FIG. 19.

FIG. 22 is a diagram illustrating another example in a case in which a measurement target is held in a petri dish.

FIG. 24 is a diagram illustrating another example in a case in which a measurement target is held in a glass slide.

DESCRIPTION OF EMBODIMENTS

Hereinafter, embodiments of an optical plate, a light irradiation apparatus, and a light measurement system according to an aspect of the present invention will be described in detail with reference to the accompanying drawings. In description of the drawings, the same elements or corresponding elements may be denoted with the same reference signs, and repeated description may be omitted. In the following drawings, a Cartesian coordinate system S may be shown.

First Embodiment

Figure 1:
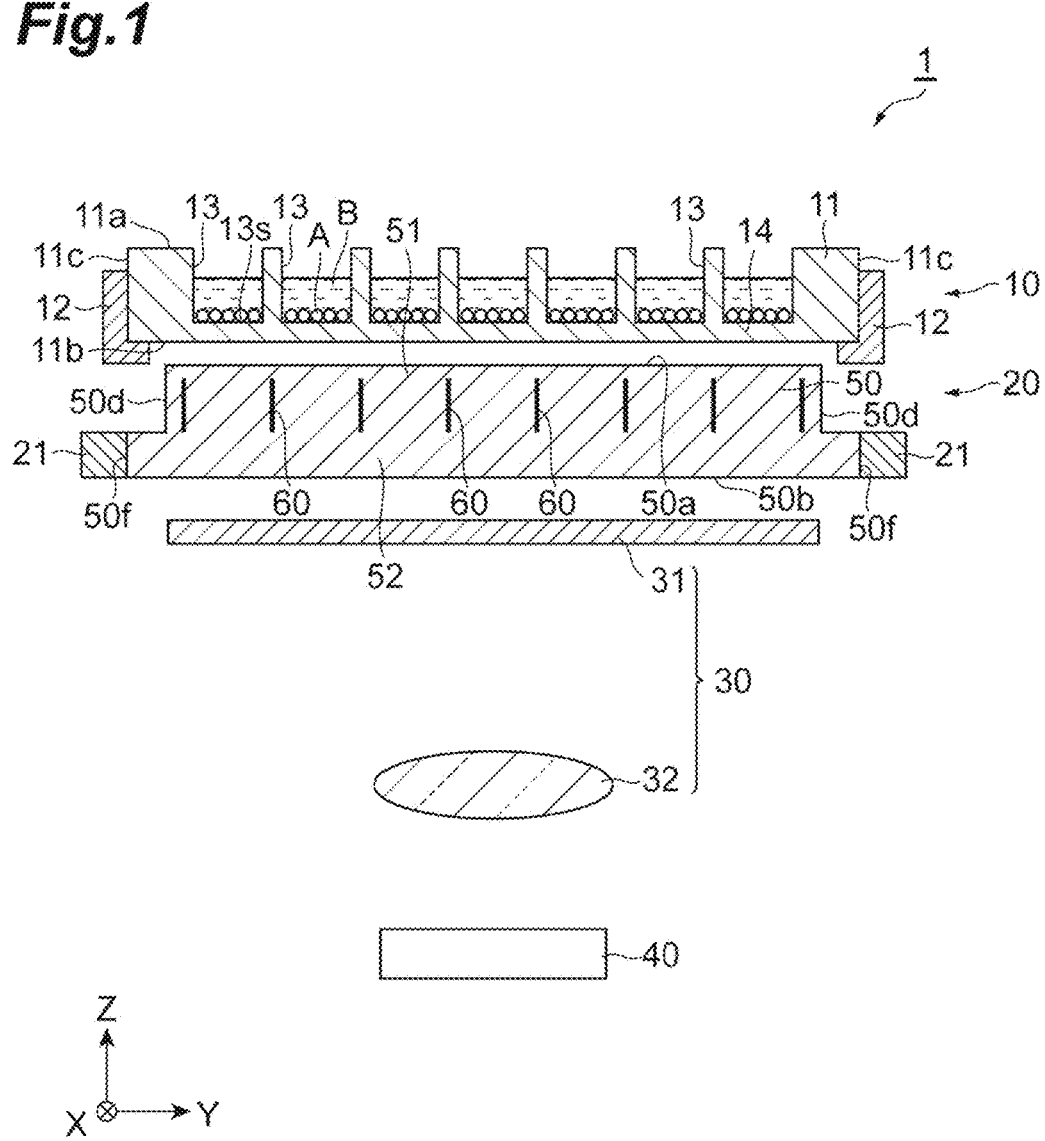
FIG. 1 is a schematic cross-sectional view illustrating a configuration of a light measurement system according to a first embodiment.

FIG. 1 is a schematic cross-sectional view illustrating a configuration of a light measurement system according to a first embodiment. As illustrated in FIG. 1, the light measurement system 1 according to the first embodiment includes a target holding mechanism 10, a light irradiation apparatus 20, an optical system 30, and an imaging device (light detector) 40. The target holding mechanism 10 includes, for example, a micro-plate (holding member) 11, and a plate holder 12 that supports the micro-plate 11.

The micro-plate 11 includes a main surface 11a, a back surface 11b opposite to the main surface 11a, and a side surface 11c which connects the main surface 11a to the back surface 11b. The back surface 11b is a surface opposite to the main surface 11a. A plurality of wells 13 arranged in a two-dimensional array in an extending direction of the main surface 11a are formed in the main surface 11a. The number of wells 13 is, for example, 96 or 384. Here, the wells 13 are rectangular cylindrical concave portions extending from the main surface 11a to the back surface 11b.

Thus, a bottom surface 13s of the well 13 is a plane substantially parallel to the main surface 11a and the back surface 11b. A bottom portion 14 of the micro-plate 11 is formed of, for example, a material such as glass, quartz, and plastic, which is a material that transmits light. Alternatively, the entire micro-plate 11 may be formed of, for example, a material such as glass, quartz, and plastic, which is a material that transmits light. The bottom portion 14 of the micro-plate 11 is a portion on the back surface 11b side relative to the bottom surface 13s of the well 13 in the micro-plate 11. Further, a shape of the bottom surface 13s of the well 13 may be a U-shape, a V-shape or a pyramid shape.

The micro-plate 11 holds a measurement target (target) A. The measurement target A is held in the well 13. The measurement target A is, for example, a cell such as stem cell, a tissue including a cell, or the like. For example, a solution B such as a culture solution, a fluorescent indicator, and a test compound is accommodated together with the measurement target A in the well 13. Here, the measurement target A is precipitated on the bottom surface 13s of the well 13. However, the measurement target A may be a floating cell or the like. In this case, the measurement target A floats in a culture solution in the well 13. The micro-plate 11 is supported by the plate holder 12 (mounted on the plate holder 12) in a state in which the micro-plate 11 holds the measurement target A as above.

The plate holder 12 supports the periphery of the micro-plate 11 so that the back surface 11b of the micro-plate 11 is exposed from the plate holder 12. More specifically, the plate holder 12 supports an outer peripheral portion of the back surface 11b and the side surface 11c so that a region opposite to the well 13 in the back surface 11b is exposed. The micro-plate 11 is manually placed on the plate holder 12. Alternatively, when the target holding mechanism 10 includes a plate loader (not illustrated), the micro-plate 11 is automatically placed on the plate holder 12 by the plate loader.

The light irradiation apparatus 20 includes an optical plate 50, and a light source 21. The optical plate 50 is for irradiating the measurement target A with light. The light source 21 is for inputting light into the optical plate 50 from a light input surface of the optical plate 50. The light source 21 is optically coupled to the light input surface (a side surface 50f) of the optical plate 50. That is, the light source 21 outputs the light to be input to the light input surface of the optical plate 50. The optical plate 50 will be described in detail below. The light source 21 is, for example, a light emitting diode (LED), a laser diode (LD), a super luminescent diode (SLD), or a lamp (for example, a xenon lamp or the like). The light source 21 is not limited to an aspect in which the light source 21 is disposed on the light input surface side of the optical plate 50 as described below. That is, the light source 21 is, for example, an aspect in which the light source 21 is disposed at any position and inputs light to the light input surface of the optical plate 50 via a light guide or the like. The measurement target A held in the micro-plate 11 is irradiated with the light from the light source 21 via the optical plate 50.

The optical system 30 transmits measurement light (for example, fluorescence, reflected light, or scattered light) from the measurement target A irradiated with light from the light source 21 via the optical plate 50 and forms an image on an imaging device 40. For this, the optical system 30 includes a wavelength selective filter 31, and a lens 32. The wavelength selective filter 31 blocks transmission of light (excitation light) with which the measurement target A is irradiated from the light source 21 via the optical plate 50, and selectively transmits the measurement light from the measurement target A. The wavelength selective filter 31 may be disposed between the lens 32 and the imaging device 40.

The wavelength selective filter 31 is, for example, a wavelength band selective filter (band pass filter), a low pass filter, or a high pass filter. In the wavelength selective filter 31, for example, a wavelength of fluorescence of a dye dying the measurement target A is selected. For example, the wavelength selective filter 31 is selected so that wavelengths of 450 nm and 560 nm are selected when the dye is a VSP that is a membrane potential sensitive dye, and a wavelength of 518 nm is selected when the dye is Fluo-4 that is a calcium ion sensitive dye. The wavelength selective filter 31 may be selected to transmit a wavelength of fluorescence of the various dyes. For example, the wavelength selective filter 31 may be selected to transmit, for example, light having a wavelength of 450 nm or more. The lens 32 is, for example, a camera lens, and converges the measurement light transmitted through the wavelength selective filter 31 and forms an image on a light receiving surface of the imaging device (imaging element) 40.

The imaging device 40 images the measurement light formed by the lens 32. The imaging device 40 is optically coupled to the back surface 50b of the optical plate 50. The imaging device 40 is, for example, an area image sensor such as a CCD image sensor or a CMOS image sensor. Further, if the imaging device 40 may be configured to detect each measurement light from each well 13, for example, a point sensor such as a photomultiplier tube, a photodiode, or an avalanche photodiode may be used.

In this embodiment, the light irradiation apparatus 20, the optical system 30, and the imaging device 40 are arranged in this order on the back surface 11b side of the micro-plate 11. Accordingly, the imaging device 40 receives, via the optical system 30, the measurement light emitted from the measurement target A irradiated with the light from the light irradiation apparatus 20, output from the back surface 11b of the micro-plate 11, transmitted through the optical plate 50, and output from the back surface of the optical plate 50, and performs imaging.

Figure 2:
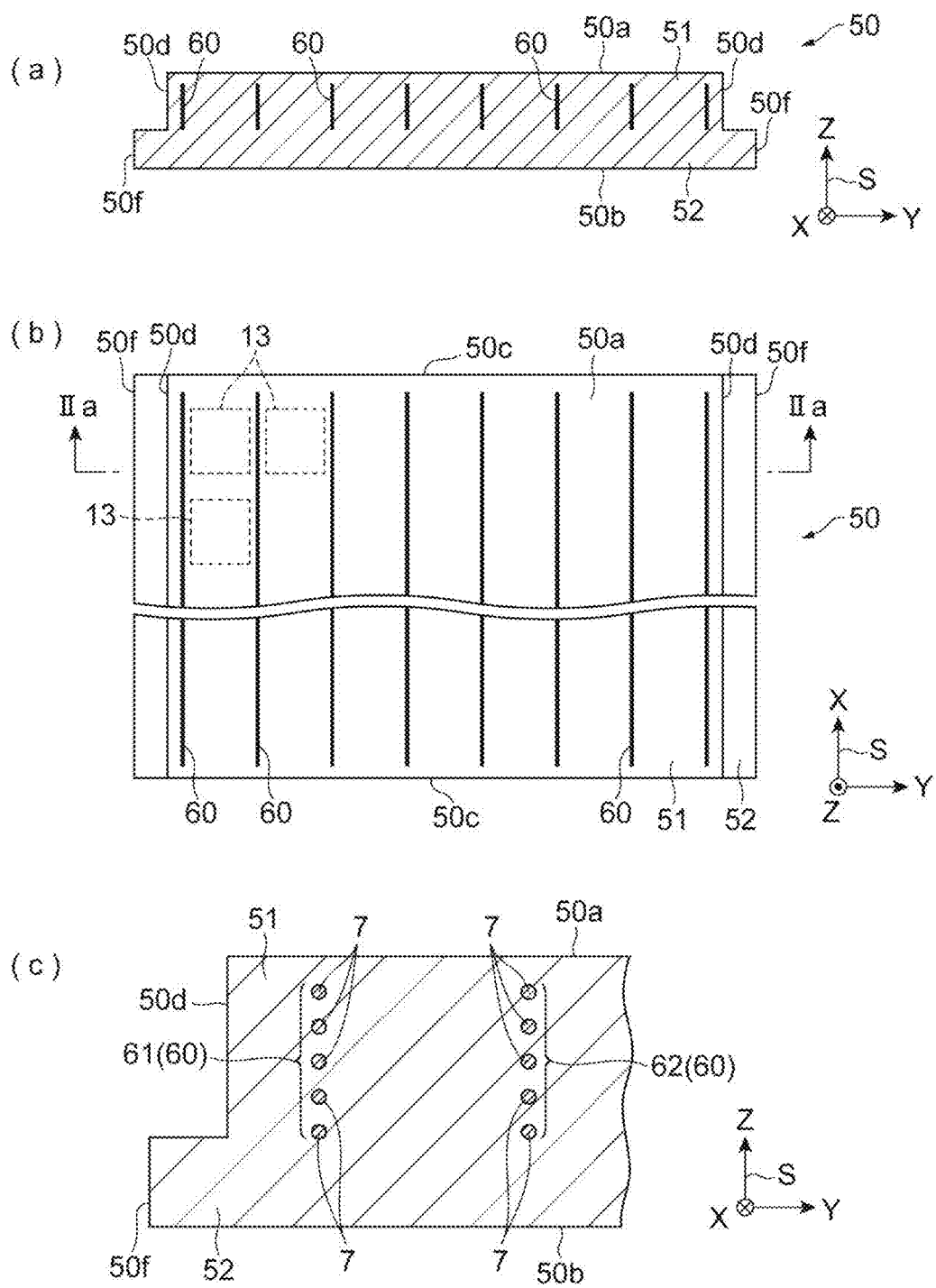
FIG. 2 is a diagram illustrating a configuration of an optical plate illustrated in FIG. 1.

Here, FIG. 2 is a diagram illustrating a configuration of the optical plate illustrated in FIG. 1. In particular, (b) of FIG. 2 is a plan view of the optical plate 50, and (a) of FIG. 2 is a cross-sectional view taken along line IIa-IIa in (b) of FIG. 2. Further, (c) of FIG. 2 is a partially enlarged view of (a) of FIG. 2. As illustrated in FIG. 2, the optical plate 50 has a substantially rectangular plate shape. The optical plate 50 includes a main surface 50a, and a back surface 50b on a side opposite to the main surface 50a. The back surface 50b is a surface opposite to the main surface 50a.

The optical plate 50 includes a first portion 51 including the main surface 50a, and a second portion 52 including the back surface 50b. The first portion 51 and the second portion 52 have a substantially rectangular plate shape. The first portion 51 and the second portion 52 may be formed integrally with each other, and may be formed separately from each other and coupled. When the first portion 51 and the second portion 52 are formed as separate bodies, for example, the first portion 51 and the second portion 52 may be fixed to each other through deposition, adhesion, or the like. Thus, the first portion 51 and the second portion 52 are optically adhered. A dimension of the first portion 51 in a first direction (here, an X-axis direction) along the main surface 50a is substantially the same as a dimension of the second portion 52 in the first direction. Thus, both end surfaces of the first portion 51 and the second portion 52 in the first direction match each other (are continuous) and constitute a side surface 50c of the optical plate 50. However, both end surfaces of the first portion 51 and the second portion 52 in the first direction may not match each other.

On the other hand, a dimension of the first portion 51 a second direction along the main surface 50a (a direction intersecting the first direction; here, a Y-axis direction) is smaller than a dimension of the second portion 52 in the second direction. Thus, both end surfaces of the first portion 51 and the second portion 52 in the second direction do not match each other, and constitute the side surfaces 50d and 50f of the optical plate 50. The side surface 50d is an end surface of the first portion 51, and the side surface 50f is an end surface of the second portion 52. The side surface 50f is substantially parallel to the side surface 50d, and is a surface that protrudes outwardly from the optical plate 50 relative to the side surface 50d. The side surfaces 50c, 50d, and 50f are surfaces between the main surface 50a and the back surface 50b. However, both end surfaces of the first portion 51 and the second portion 52 in the second direction may match each other (be continuous) and constitute the side surfaces of the optical plate 50.

As illustrated in FIG. 1, here, the light source 21 is disposed in contact with the side surface 50f Accordingly, in the optical plate 50, the side surface 50f is a light input surface for inputting light (input light) to the inside of the optical plate 50. However, the side surface 50d or the side surface 50c may be the light input surface. Meanwhile, the optical plate 50 is disposed so that the main surface 50a faces the measurement target A held in the micro-plate 11 (the back surface 11b of the micro-plate 11). Accordingly, in the optical plate 50, the main surface 50a facing the measurement target A is a light output surface for outputting light (output light) from the optical plate 50 toward the measurement target A.

Here, a plurality of light diffusion portions 60 are formed in the optical plate 50. Here, the light diffusion portions 60 are formed inside the optical plate 50. In particular, the light diffusion portions 60 are formed in the first portion 51 and are not formed in the second portion 52. That is, the first portion 51 is a portion in which the light diffusion portions 60 are formed, and the second portion 52 is a portion in which the light diffusion portions 60 are not formed. The portion in which the light diffusion portions 60 are not formed is, for example, a portion in which there is no light diffusion portion 60 between the end surfaces that face each other. The light diffusion portion 60 outputs the light input from the side surface 50f to the inside of the optical plate 50 from the main surface 50a that is a light output surface to the outside of the optical plate 50 while diffusing (for example, scattering or refracting) the light. That is, the light diffusion portion 60 is for diffusing the light inside the optical plate 50. On the other hand, the second portion 52 functions as a light guide portion that guides light without diffusing the light between a pair of side surfaces 50f and 50f that face each other. That is, the light guide portion is formed in the second portion 52. Thus, by providing the portion in which there is no light diffusion portion 60 between the end surfaces facing each other, it is possible to output the light from the light output surface such that a light intensity along the light output surface (in this case, main surface 50a) is substantially uniform.

The light diffusion portion 60 extends between a pair of side surfaces 50c and 50c in a first direction (an X-axis direction). Further, the light diffusion portions 60 are arranged at substantially equal intervals in a second direction (a Y-axis direction). The interval of the arrangement of the light diffusion portions 60 is defined according to the measurement target A. The interval of the arrangement of the light diffusion portions 60 is defined according to, for example, a dimension and an arrangement of the wells 13 in the second direction. More specifically, the light diffusion portions 60 are arranged to be alternate with the wells 13 (to sandwich the wells 13) when viewed in a third direction (in this case, a Z-axis direction) intersecting the first and second directions. Accordingly, most of the light diffusion portion 60 are arranged to be located between the wells 13 adjacent to each other when viewed in the third direction. In other words, the micro-plate 11 is disposed so that the light diffusion portions 60 are arranged as above.

Here, the light diffusion portion 60 extends in the third direction. More specifically, the light diffusion portion 60 extends with a predetermined length in a thickness direction (the third direction) of the optical plate 50 from the main surface 50a toward the back surface 50b. That is, the light diffusion portion 60 is formed to extend over a portion between the main surface 50a and the back surface 50b. Such a light diffusion portion 60 is formed by converging laser light on a member (hereinafter referred to as "object to be processed") serving as a base of the optical plate 50.

Figure 3:
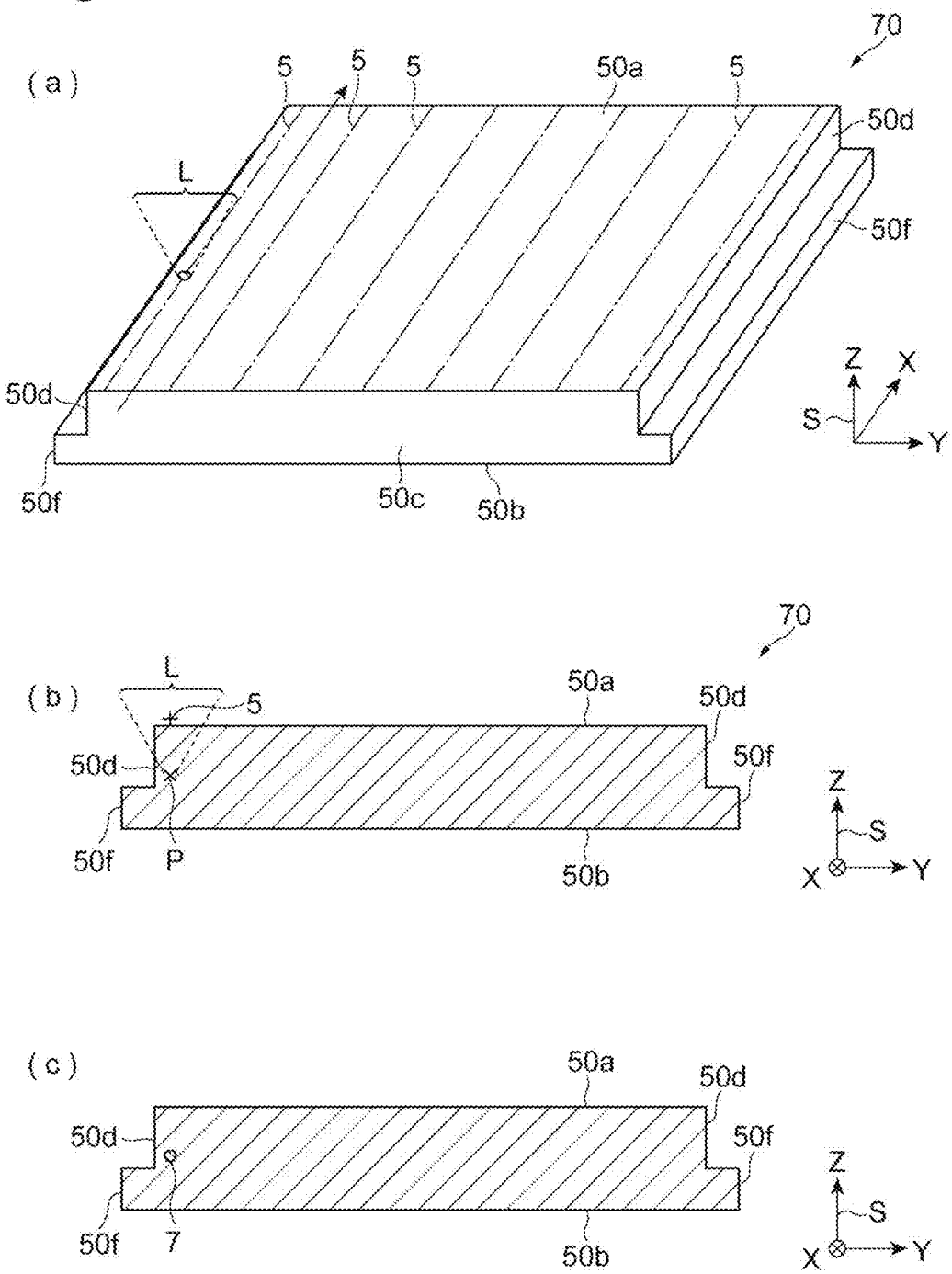
FIG. 3 is a diagram illustrating main processes of a method of forming a light diffusion portion.

An example of a method of forming the light diffusion portions 60 will be described. A specific procedure of forming the light diffusion portions 60 is not limited to the following example. First, a object to be processed 70 serving as a source of the optical plate 50 (or the first portion 51) is prepared, as illustrated in (a) of FIG. 3. In the object 70, a plurality of (for example, virtual) lines to cut 5 are set to correspond to positions in which the light diffusion portions 60 are set. Subsequently, for example, the main surface 50a of the object 70 is set as an input surface of the laser light L, and a converging point P of the laser light L is located in a predetermined position (a predetermined depth) in the third direction, as illustrated in (b) of FIG. 3. The converging point P is a place at which the laser light L is converged.

In this state, the converging point P of the laser light L is moved in the first direction along the line 5 relative to the object 70 (that is, scanning is performed using the laser light L in the first direction). Thus, a line of modified region 7 is formed in the first direction inside the object 70, as illustrated in (c) of FIG. 3. This modified region 7, for example, constitutes the light diffusion portion 60 (the first light diffusion portion 61 in FIG. 2) that is located on an outermost side (on the side surface 50d side) of the optical plate 50 in the second direction.

Subsequently, the position of the converging point P of the laser light L is shifted in the second direction while maintaining a position in the third direction of the converging point P of the laser light L to be a predetermined position (a predetermined depth), as illustrated in (a) of FIG. 4. In this state, the scan is performed again using the laser light L in the first direction along another line 5 (the converging point P is relatively moved), as illustrated in (b) of FIG. 4. Thus, another line of modified region 7 is formed in the first direction, as illustrated in (c) of FIG. 4. This modified region 7 constitutes, for example, the light diffusion portion 60 (the second light diffusion portion 62 in FIG. 2) adjacent to the first light diffusion portion 61.

Thus, the scan is performed using the laser light L in the first direction along each of the lines 5 while changing the position of the converging point P of the laser light L in the second direction (without changing the position of the converging point P of the laser light L in the third direction). After the scan using the laser light L along all the lines 5 is completed, the position in the third direction of the converging point P of the laser light L is shifted to the main surface 50a side (that is, the input surface side of the laser light L), and the same process is repeated. Thus, a plurality of light diffusion portions 60 formed of a plurality of lines of the modified regions 7 arranged in the third direction are formed to extend in the first direction and arranged in the second direction, as illustrated in FIG. 2. As a result, the optical plate 50 is fabricated.

Here, the modified region 7 may be continuously formed or may be intermittently formed. Further, the modified regions 7 may have a line shape or may have a point shape. The modified region 7 may be formed at least inside the object 70. Further, cracks may occur from the modified region 7, and the cracks and modified region 7 may be exposed on an outer surface (for example, the main surface 50a) of the object 70.

Further, here, the laser light L is transmitted through the object 70 and particularly absorbed near the converging point P inside of the object 70. Accordingly, the modified region 7 is formed in the object 70 (that is, internal absorption type laser processing). Therefore, since the laser light L is hardly absorbed on the main surface 50a of the object 70, the main surface 50a of the object 70 is not melted. In general, when a hole or a groove is formed due to melting and removal from the main surface 50a (surface absorption type laser processing), a processing region gradually progresses from the main surface 50a side to the back surface 50b side.

The modified region 7 formed in this embodiment refers to a region in which a density, a refractive index, a mechanical strength, or other physical properties is different from those in surroundings. Examples of the modified region 7 are a molten processed region, a crack region, an insulation breakdown region, a refractive index changed region, and their mixed regions. Further examples of the modified region 7 include an area where the density has changed from that of an unmodified region in a material of the object 70 and an area formed with a lattice defect (which may collectively be referred to as a high-density transitional region).

Further, the molten processed regions, refractive index changed regions, areas where the modified region has a density different from that of the unmodified region, or areas formed with a lattice defect may further incorporate a fracture (fissure or microcrack) therewithin or at an interface between the modified region 7 and an unmodified region. The incorporated fracture may be formed over the whole surface of the modified region 7 or in only a part or a plurality of parts thereof.

Further, in this embodiment, the modified region 7 is formed by forming a plurality of modified spots (processing marks) along the lines 5. The modified spot is a modified portion formed by a shot of one pulse of pulsed laser light (that is, one pulse laser irradiation: laser shot) and becomes the modified region 7 by collecting modified spots (or alone). Examples of the modified spot may include a crack spot, a molten processed spot, a refractive index changed spot, or a spot in which at least one of these is combined. The modified region 7 shown in a section in (c) of FIG. 2, (c) of FIG. 3, and (c) of FIG. 4 is, for example, the modified spot.

The modified region 7 may be formed in a linear shape by coupling linear modified spots extending in the first direction. In this case, the linear modified spot along a long axis can be formed by using laser light L of a beam spot having a shape with a long axis at a converging point P. Further, a direction of extension of the linear modified spot can be adjusted by adjusting a direction of the long axis of the beam spot of the laser light L at the converging point P.

An example of laser processing conditions when the modified region 7 (that is, the light diffusion portion 60) is formed in this embodiment are as follows.

Figure 5:
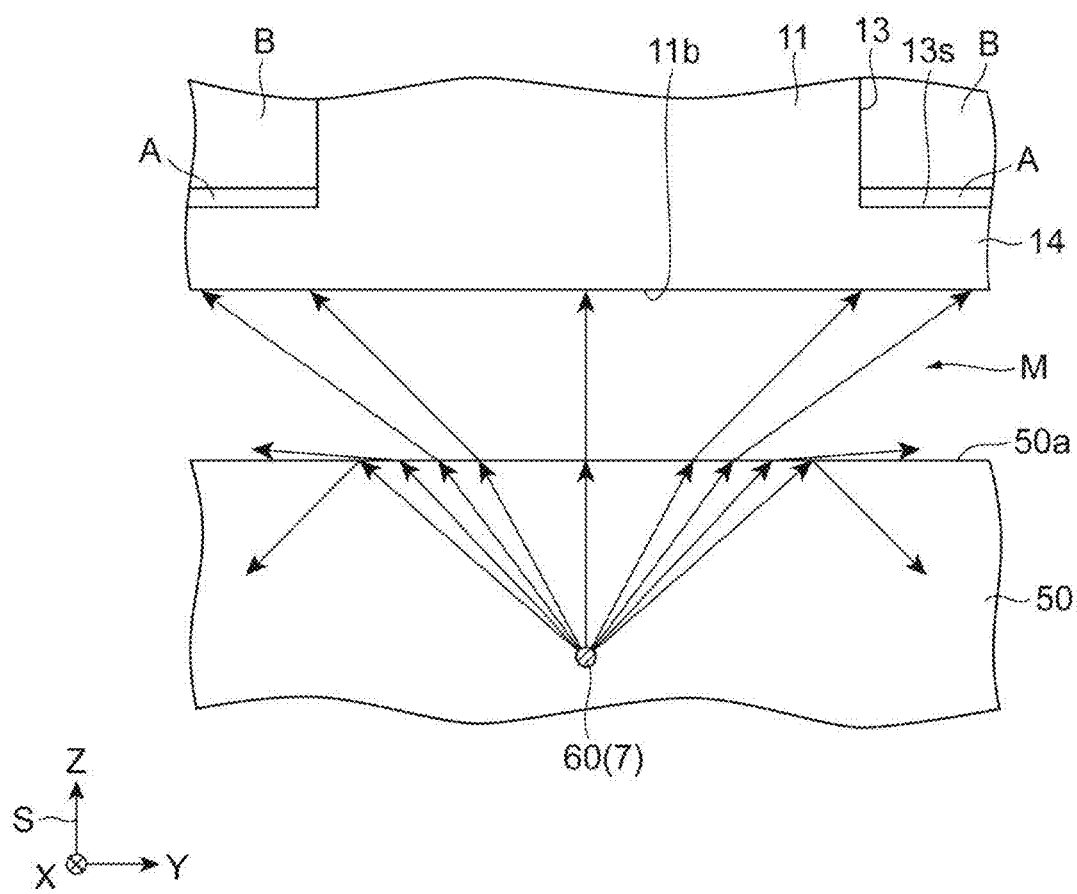
FIG. 5 is a schematic cross-sectional view illustrating a state in which light is diffused in the light diffusion portion.

Laser light source: semiconductor laser excitation Yb: KGW laser
Wavelength of the laser light L: 1030 nm
Repetition frequency of the laser light L: 50 kHz
Pulse width of the laser light L: 350 fs
Output of the laser light L: 10 µJ/pulse FIG. 5 is a schematic cross-sectional view illustrating a state in which light is diffused in the light diffusion portion. In FIG. 5, an optical path is indicated by an arrow. Further, in FIG. 5, for ease of description, a case in which the light diffusion portion 60 includes a single modified region 7 (modified spot) in a third direction is illustrated. As illustrated in FIG. 5, light input to the optical plate 50 and reaching the light diffusion portion 60 is diffused in each direction in the light diffusion portion 60.

In the light diffused in the light diffusion portion 60, the light input to the main surface 50a at a relatively small angle is output from the main surface 50a while being refracted on the main surface 50a. The light output from the main surface 50a propagates in an intermediate layer M (an air layer, for example) between the micro-plate 11 and the optical plate 50 and is input to the micro-plate 11 from the back surface 11b of the micro-plate 11. The light input to the micro-plate 11 is radiated to the measurement target A held in the well 13. Measurement light (for example, fluorescence, reflected light, or scattered light) from the measurement target A generated due to the measurement target A being irradiated with the light is transmitted through the main surface 50a and the back surface 50b and is detected by the imaging device 40.

Here, it is assumed that the refractive index of the intermediate layer M is smaller than the refractive index of the optical plate 50. Accordingly, the light diffused in the light diffusion portions 60 is refracted to be more widely diffused between the main surface 50a and the intermediate layer M (that is, refracted at an increasing angle with respect to the depth direction of the well 13) and radiated to the measurement target A. On the other hand, in the light diffused in the light diffusion portions 60, the light input to the main surface 50a at a relatively large angle is totally reflected in the main surface 50a and is not output from the main surface 50a. The light totally reflected on the main surface 50a propagates inside the optical plate 50 and is diffused in another light diffusion portion 60 again. A material of the optical plate 50 is synthetic quartz having a refractive index of about 1.464, and when a material of the intermediate layer M is air having a refractive index of about 1.00, a critical angle at which the total reflection occurs on the main surface 50a is about 43°.

Here, an embodiment of a light irradiation method and a light measurement method will be described. In the light irradiation method according to this embodiment, the optical plate 50 is used as described above. That is, in the light irradiation method according to this embodiment, the measurement target A (target) is irradiated with the light using the optical plate 50 including the main surface 50a (light output surface) for outputting the light, the back surface 50b opposite to the main surface 50a, the side surface 50f (light input surface) that is a surface between the main surface 50a and the back surface 50b and for inputting the light, and the light diffusion portions 60 formed by converging the laser light L.

More specifically, in the light irradiation method according to this embodiment, first, light is input to the side surface 50f using the light source 21 and input to the optical plate 50 from the side surface 50f. The light input to the optical plate 50 is guided in the inside of the optical plate 50. The light guided in the inside of the optical plate 50 and reaching the light diffusion portion 60 is diffused in the light diffusion portion 60. At least portion of the light diffused in the light diffusion portion 60 (the light input to the main surface 50a at a relatively small angle) is output from the main surface 50a and radiated to the measurement target A.

That is, the light irradiation method according to this embodiment includes a light input step of inputting light to the side surface 50f, a light diffusion step of diffusing the light input from the side surface 50f in the light diffusion portion 60, a light output step of outputting the light diffused in the light diffusion portion 60 from the main surface 50a, and a light irradiation step of irradiating the measurement target A with the light output from the main surface 50a. Further, the light irradiation method according to this embodiment may include a light guide step of guiding the light input from the side surface 50f inside the optical plate 50.

Further, the light measurement method according to this embodiment further includes detecting (imaging) the measurement light (fluorescence, reflected light, or scattered light) from the measurement target A irradiated with the light from the optical plate 50 using a light detector (imaging device 40) after the light irradiation method described above. In particular, here, the measurement light from the measurement target A transmitted through the main surface 50a and the back surface 50b is detected. That is, the light measurement method according to this embodiment further includes a light detection step of detecting the measurement light from the measurement target A transmitted through the main surface 50a and the back surface 50b, in addition to the respective steps of the light irradiation method described above.

FIG. 6 is a diagram illustrating a relationship between a configuration of the light diffusion portion and an intensity distribution of light output from the optical plate. (a) of FIG. 6 illustrates a case in which the light diffusion portion 60 includes a single modified region 7 (modified spot) in a third direction, as in FIG. 5. Further, (b) of FIG. 6 illustrates a case in which the light diffusion portions 60 include a plurality of modified regions (modified spots) 7 in the third direction, as in (c) of FIG. 2. That is, (b) of FIG. 6 illustrates a case in which the light diffusion portion 60 extends with a predetermined length in a thickness direction (third direction) of the optical plate 50 from the main surface 50a to the back surface 50b.

As illustrated in (a) of FIG. 6, when the light diffusion portion 60 includes a single modified region 7 in the third direction, an intensity distribution is attenuated with an increasing distance from a center position (in a second direction) corresponding to the light diffusion portion 60. On the other hand, when the light diffusion portions 60 include a plurality of modified regions 7 in the third direction, light toward the third direction from one of the modified regions 7 of the light diffusion portions 60 is diffused again when passing through another modified region 7, as illustrated in (b) of FIG. 6. Therefore, in this case, the intensity is degraded in a central position (in the second direction) corresponding to the light diffusion portion 60, but it is possible to improve the intensity on both sides thereof. That is, by adjusting the length of the light diffusion portion 60 extending in the third direction from the main surface 50a to the back surface 50b, it is possible to adjust the light intensity in a central position (in the second direction) corresponding to the light diffusion portion 60 and on both sides thereof.

Figure 7:
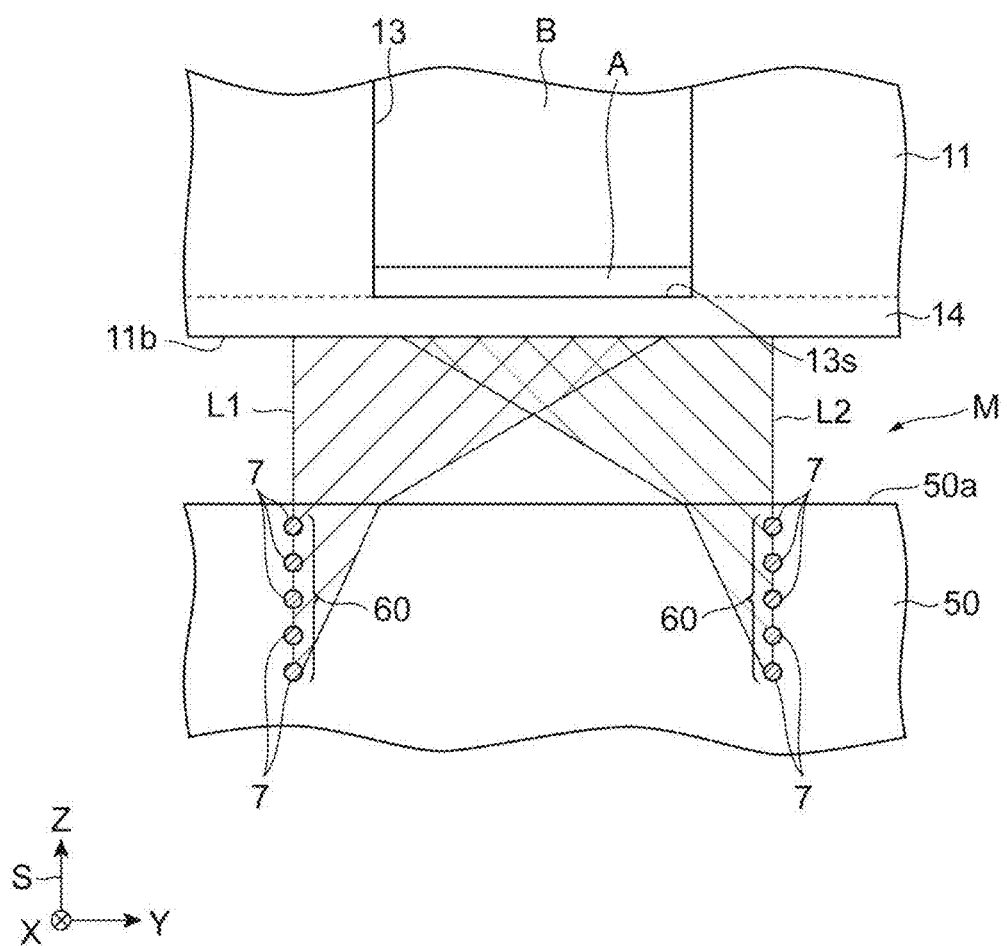
FIG. 7 is a schematic cross-sectional view illustrating a state in which a measurement target is irradiated with light from a pair of light diffusion portions adjacent to each other.

FIG. 7 is a schematic cross-sectional view illustrating a state in which a measurement target is irradiated with light from a pair of light diffusion portions adjacent to each other. As illustrated in FIGS. 2 and 7, here, the light diffusion portions 60 are disposed on both sides of the well 13 when viewed in the third direction. Therefore, the measurement target A held in the well 13 is irradiated with light L1 diffused in one of the light diffusion portions 60 and output from the main surface 50a of the optical plate 50 and light L2 diffused in the other of the light diffusion portions 60 and output from the main surface 50a of the optical plate 50 to be superposed on each other. In other words, the measurement target A can be irradiated with the lights L1 and L2 from an outer side of the well 13 when viewed in the third direction. Therefore, oblique illumination (that is, illumination based on a dark field) can be preferably performed with respect to the measurement target A.

FIG. 8 is a diagram illustrating a simulation result of a light intensity distribution when viewed in the third direction. FIG. 8 illustrates a magnitude of light intensity using shades of color. (a) of FIG. 8 is a diagram illustrating a distribution of intensity of light output from optical plate 50, and (b) of FIG. 8 is a diagram illustrating a distribution of light intensity in a state in which the micro-plate 11 is arranged on the optical plate 50. As illustrated in FIG. 8, according to the optical plate 50 of this embodiment, it is possible to irradiate a plurality of wells 13 with light with generally uniform intensity.

As described above, the light measurement system 1 according to this embodiment includes the light irradiation apparatus 20 having the optical plate 50. The optical plate 50 includes the light diffusion portions 60 that outputs the light input from the side surface 50f (light input surface) from the main surface 50a (light output surface) while diffusing the light input from the side surface 50*f* (light input surface). Accordingly, if the optical plate 50 is arranged so that the main surface 50*a* (light output surface) faces the measurement target A, it is possible to uniformly irradiate the measurement target A with the light diffused in the light diffusion portions 60. In particular, in the optical plate 50, the light diffusion portion 60 is formed by converging the laser light L on a member serving as the optical plate 50 (the object 70) (that is, by performing laser processing on the member). Therefore, it is easy for the light diffusion portion 60 to be formed, and it is possible to perform light irradiation according to irradiation conditions such as a shape of the measurement target A (for example, a shape, a size, and an arrangement of the wells 13).

Figure 9:
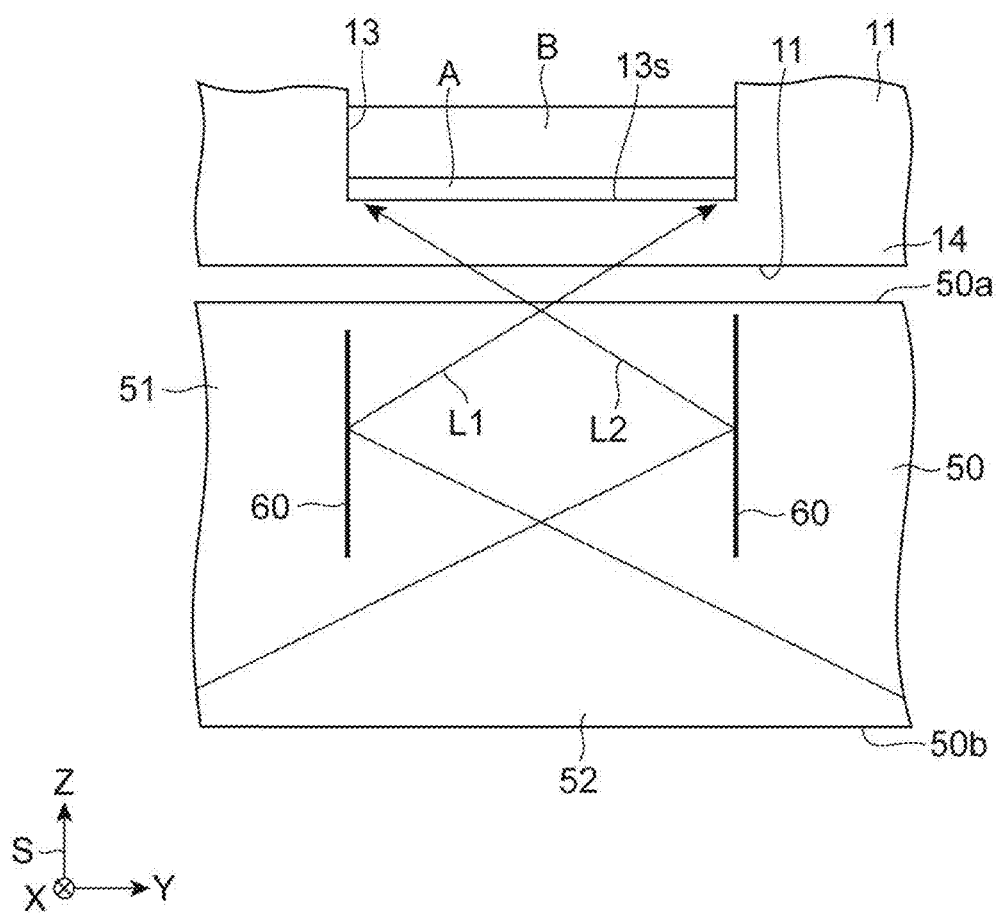
FIG. 9 is a schematic cross-sectional view illustrating a state in which a measurement target is irradiated with light diffused in a light diffusion portion.

Further, in the light measurement system 1 according to this embodiment, the light diffusion portions 60 extending in the third direction intersecting (substantially perpendicular to) the main surface 50*a* of the optical plate 50 are formed in the optical plate 50, as illustrated in FIG. 9. Therefore, it is possible to increase the amount of light output from regions adjacent to the light diffusion portions 60. The regions adjacent to the light diffusion portion 60 are, for example, regions on both sides of the light diffusion portion 60 overlapping the wells 13 in a case in which the light diffusion portion 60 is linearly formed to be located between the wells 13 when viewed in the third direction, as described above. Alternatively, the region adjacent to the light diffusion portion 60 is, for example, an annular region on an outer side of the light diffusion portion 60 overlapping the wells 13 in a case in which the light diffusion portions 60 are formed to surround the wells 13 when viewed in the third direction, as will be described below. The light diffusion portions 60 are disposed to sandwich (to surround) the well 13 when viewed in the third direction. The lights L1 and L2 input to the optical plate 50 are diffused in the light diffusion portions 60, output from the main surface 50*a* of the optical plate 50, and then, input to the well 13 from the bottom surface 13*s* of the well 13 of the micro-plate 11.

Therefore, the lights L1 and L2 directed to the well 13 are input to the well 13 at an incidence angle smaller than 90° with respect to the bottom surface 13*s* of the well 13. Further, the lights L1 and L2 relatively strongly illuminate the bottom surface 13*s* of the well 13. In other words, the measurement target A precipitated on the bottom surface 13*s* of the well 13 is mainly irradiated with the lights L1 and L2. Therefore, background light noise caused by the irradiation of the solution B of the well 13 with the light from the optical plate 50 is reduced.

Here, the optical plate 50 includes the second portion 52 functioning as a light guide portion for guiding light between the side surface (light input surfaces) 50*f* and 50*f* that face each other. Therefore, the light input from the side surface 50*f* is diffused in the light diffusion portions 60 and output while being guided between the side surfaces 50*f* and 50*f* by the second portion 52 serving as the light guide portion. Therefore, it is possible to more uniformly irradiate the measurement targets A present at various places in the region in which the optical plate 50 is disposed, with the light.

Further, the optical plate 50 may include the first portion 51 in which the light diffusion portions 60 are formed, and the second portion 52 which is formed integrally with the first portion 51 and in which the light diffusion portions 60 are not formed, and the light guide portion may be formed in the second portion 52. In this case, if laser processing is controlled such that the light diffusion portions 60 are not formed in the second portion 52 among the first portion 51 and the second portion 52 formed integrally with each other, the light guide portion is formed of the second portion 52. That is, in this case, the light guide portion can be formed inside the optical plate 50 through the control of the laser processing.

Alternatively, the optical plate 50 may be formed by optically coupling the first portion 51 in which the light diffusion portions 60 are formed to the second portion 52 that is formed separately from the first portion 51 and in which light diffusion portions 60 are not formed, and the light guide portion may be formed of the second portion 52. In this case, if the first portion 51 in which the light diffusion portions 60 are formed and the second portion 52 in which the light diffusion portions are not formed are prepared and optically coupled to each other using laser processing, the light guide portion can be formed of the second portion 52.

Figure 10:
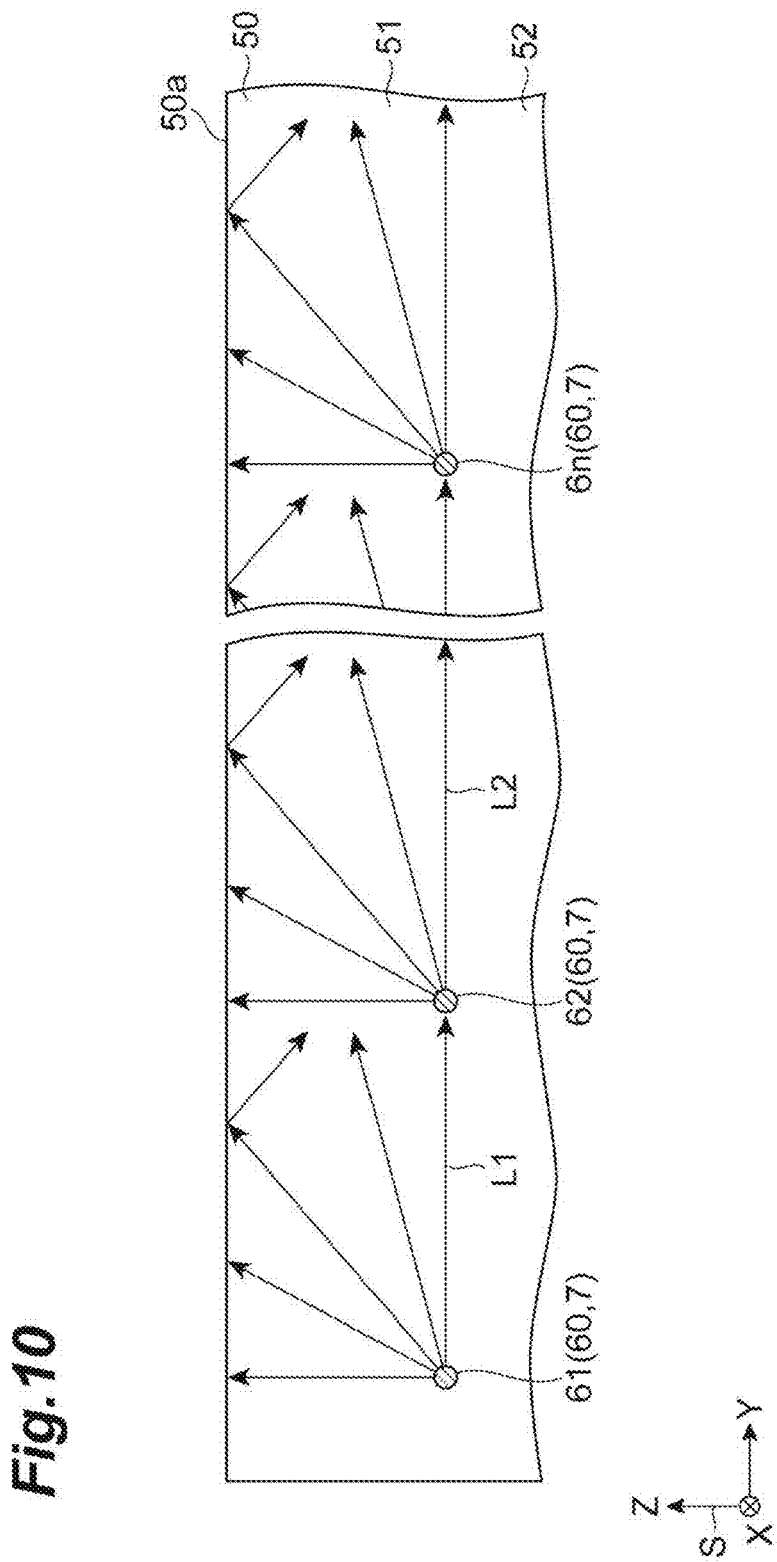
FIG. 10 is a schematic cross-sectional view illustrating a state in which light is sequentially diffused by a plurality of light diffusion portions.

Here, an operation between the light diffusion portions 60 will be described. FIG. 10 is a schematic cross-sectional view illustrating a state in which light is sequentially diffused by a plurality of light diffusion portions. As illustrated in FIG. 10, the light input to the optical plate 50 is assumed to be first diffused by the first light diffusion portion 61. The light first diffused in the first light diffusion portion 61 is referred to as first diffused light. Light L1 of a portion of the first diffused light is continuously diffused in the second light diffusion portion 62 adjacent to the first light diffusion portion 61. The light diffused in the second light diffusion portion 62 as above is referred to as a secondary diffused light. Further, light L2 of a portion of the second diffused light is sequentially diffused in the plurality of light diffusion portions 60. For example, light further diffused in an n-th light diffusion portion 6*n* is referred to as n-order diffused light.

Light output from the main surface 50*a* of the optical plate 50 and supplied for illumination of the measurement target A is influenced by high-order diffused light including second diffused light to n-th diffused light, in addition to the first diffused light. Therefore, in order to reduce uneven irradiation with respect to the measurement target A, high-order diffused light including secondary diffused light to n-th order diffused light may be reduced or high-order diffusion including second diffusion to n-order diffusion may uniformly occur in the entire optical plate 50.

Figure 11:
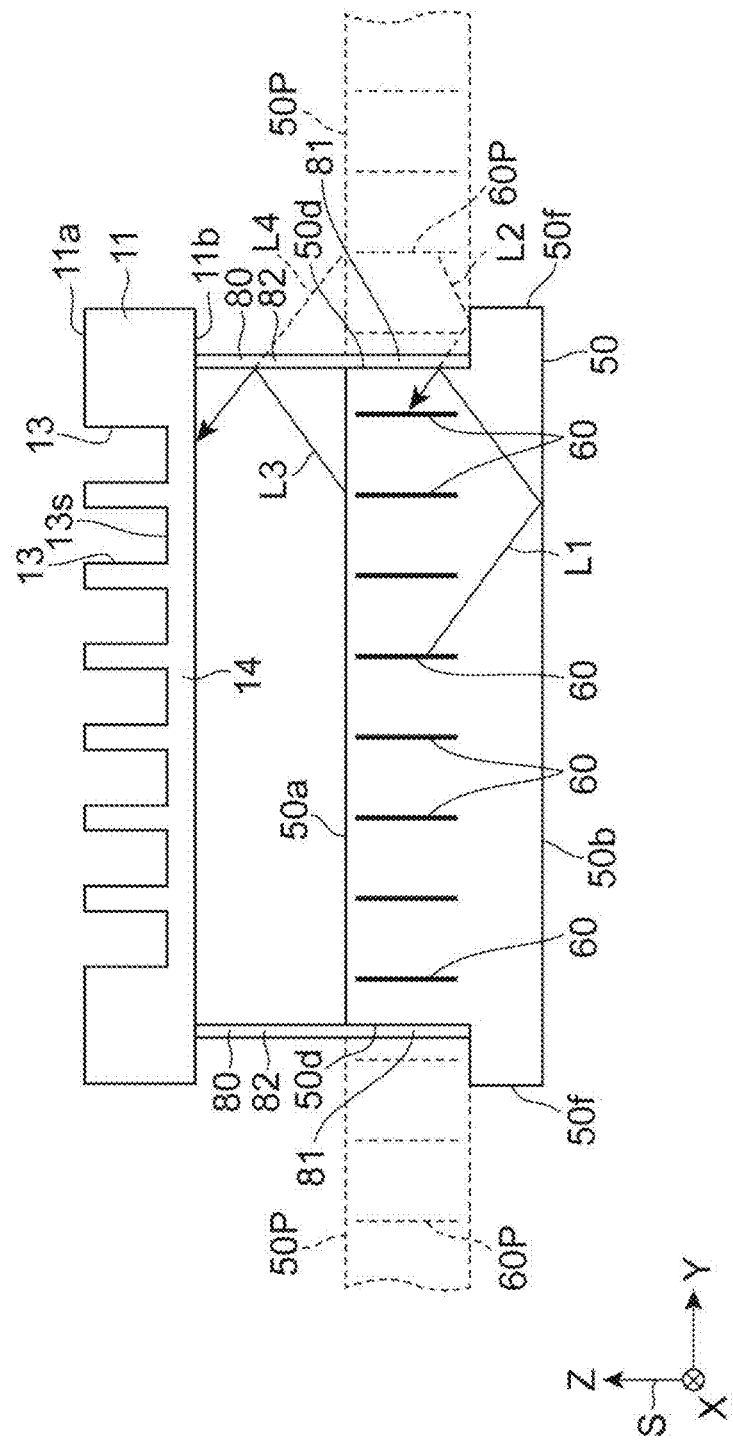
FIG. 11 is a schematic cross-sectional view illustrating an example of an optical plate further including a reflective portion.

Therefore, the optical plate 50 may further have a pair of reflective portions 80, as illustrated in FIG. 11. The reflective portion 80 extends in the third direction intersecting the main surface 50*a* that is a light output surface of the optical plate 50. The reflective portion 80 reflects at least light from the light source 21. The reflective portion 80 includes a first reflective region 81 disposed on the side surface 50*d* of the optical plate 50, and a second reflective region 82 protruding in the third direction from the main surface 50*a*.

When the reflective portion 80 has the first reflective region 81, for example, the light L1 diffused in the predetermined light diffusion portion 60 and input to the side surface 50*d* is reflected by the first reflective region 81 and then diffused in another light diffusion portion 60. This corresponds to the light L1 being regarded as light L2 diffused in a pseudo light diffusion portion 60P by forming a pseudo light diffusion portion 60 (light diffusion portion 60P) at a position at which the light L1 reflected in the first reflective region 81 is swept. That is, the first reflective region 81 causes pseudo high-order diffusion. Therefore, it is possible to reduce uneven irradiation with respect to the measurement target A due to uniform high-order diffusion in the entire optical plate 50. In order to form the first reflective region 81, a method of providing a reflective member such as a mirror on the side surface 50*d* or a method of performing a reflection process on the side surface 50*d* is used.

On the other hand, if the reflective portion 80 has the second reflective region 82, for example, the light L3 that is diffused in the predetermined light diffusion portion 60, is output from the main surface 50*a*, and then originally deviates from the measurement target A is reflected by the second reflective region 82 and radiated to the measurement target A. This corresponds to an optical plate 50 (optical plate 50P) being caused to be a pseudo one at a position at which the light L3 reflected at the second reflective region 82 is swept and the measurement target A being irradiated with light L4 from the pseudo-optical plate 50P. Thus, it is possible to further reduce uneven irradiation. In order to form the second reflective region 82, a method of providing a reflective member such as a mirror to protrude in the third direction from the main surface 50*a* is used.

Figure 12:
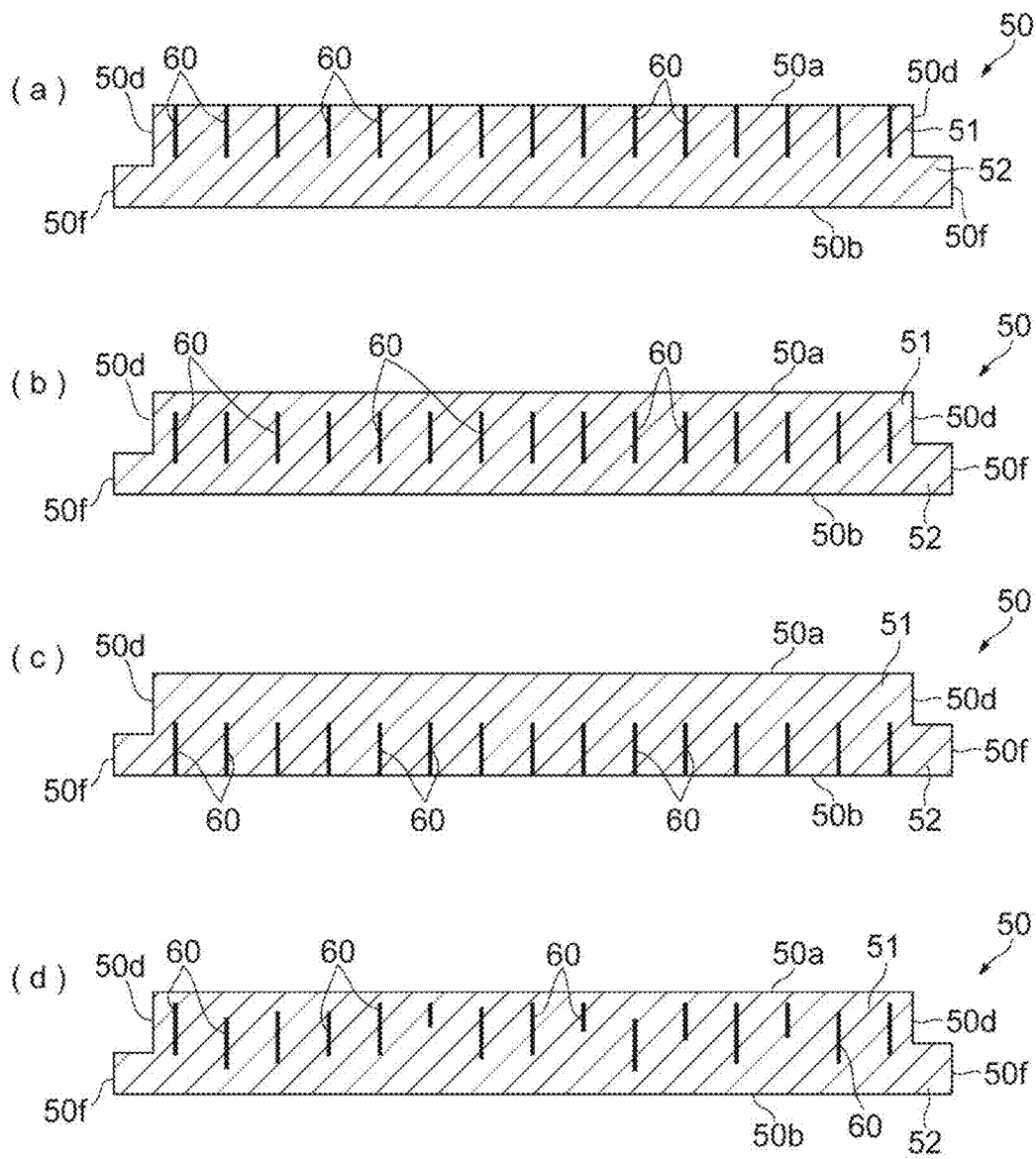
FIG. 12 is a cross-sectional view illustrating a modification example of the optical plate.

Various modifications may be performed on the optical plate 50 described above. FIG. 12 is a cross-sectional view illustrating a modification example of the optical plate. As illustrated in (a) of FIG. 12, in the optical plate 50, the light diffusion portions 60 may be formed to reach the main surface 50*a* and not to reach the back surface 50*b*. That is, the light diffusion portion 60 may be formed at least inside the optical plate 50.

Further, in the optical plate 50, the light diffusion portions 60 may be formed only in the optical plate 50 to extend from the first portion 51 to the second portion 52, as illustrated in (b) of FIG. 12. In this case, the light guide portion is formed in the second portion 52. More specifically, in this case, a portion on the back surface 50*b* side in which the light diffusion portions 60 are not formed in the second portion 52 functions as a light guide portion that guides light between a pair of side surfaces 50*f* and 50*f* facing each other.

Further, in the optical plate 50, the light diffusion portions 60 may be formed to reach the back surface 50*b* and not to reach the main surface 50*a*, as illustrated in (c) of FIG. 12. In this case, for example, the light source 21 may be disposed on the side surface 50*d* that is an end surface of the first portion 51, and the side surface 50*d* may be a light input surface for inputting light to the optical plate 50. In this case, a portion on the main surface 50*a* side in which the light diffusion portions 60 are not formed in the first portion 51 may function as a light guide portion that guides light between a pair of side surfaces 50*d* and 50*d* that face each other. In other words, in this case, the first portion 51 corresponds to a portion (the second portion 52 described above) in which the light guide portion is formed. Further, in this case, the second portion 52 corresponds to a portion (the first portion 51 described above) in which the light diffusion portion 60 is formed. Further, the back surface 50*b* may be the light output surface for outputting the light.

Further, a formation position in the third direction and a length in the third direction may be set at random for each light diffusion portion 60, as illustrated in (d) of FIG. 12.

Figure 13:
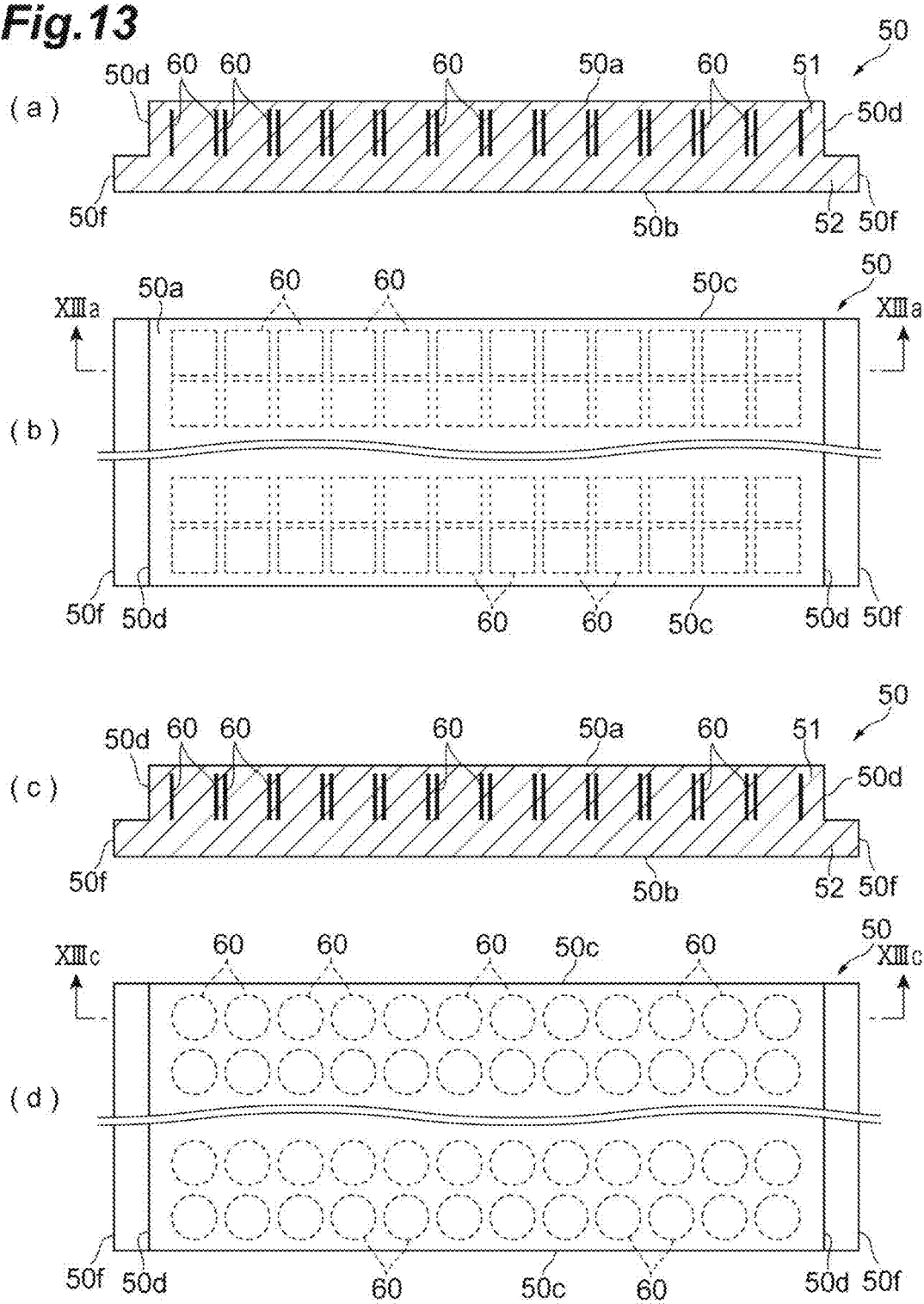
FIG. 13 is a diagram illustrating a modification example of the optical plate.

Next, a modification example of the optical plate 50 will be described. FIG. 13 is a diagram illustrating a modification example of the optical plate. (a) of FIG. 13 is a cross-sectional view taken along line XIIIa-XIIa in a plan view of (b) of FIG. 13. Further, (c) of FIG. 13 is a cross-sectional view taken along line XIIIc-XIIIc in a plan view of (d) of FIG. 13. As illustrated in FIG. 13, in the optical plate 50, the light diffusion portion 60 can be formed to correspond to a shape of the well 13 of the micro-plate 11 that holds the measurement target A.

For example, in a case in which the wells 13 of the micro-plate 11 are rectangular cylindrical concave portions arranged in a two-dimensional array, the light diffusion portions 60 may be formed in a rectangular cylindrical shape along an outer shape of each well 13, as illustrated in (a) and (b) of FIG. 13. Alternatively, in a case in which the wells 13 of the micro-plate 11 are columnar concave portions arranged in a two-dimensional array, the light diffusion portions 60 may be formed in a cylindrical shape along the outer shape of each well 13, as illustrated in (c) and (d) of FIG. 13. In a case in which such light diffusion portions 60 are formed, an arrangement of the optical plate 50 and the micro-plate 11 may be set so that one light diffusion portion 60 is disposed for each well 13.

Figure 14:
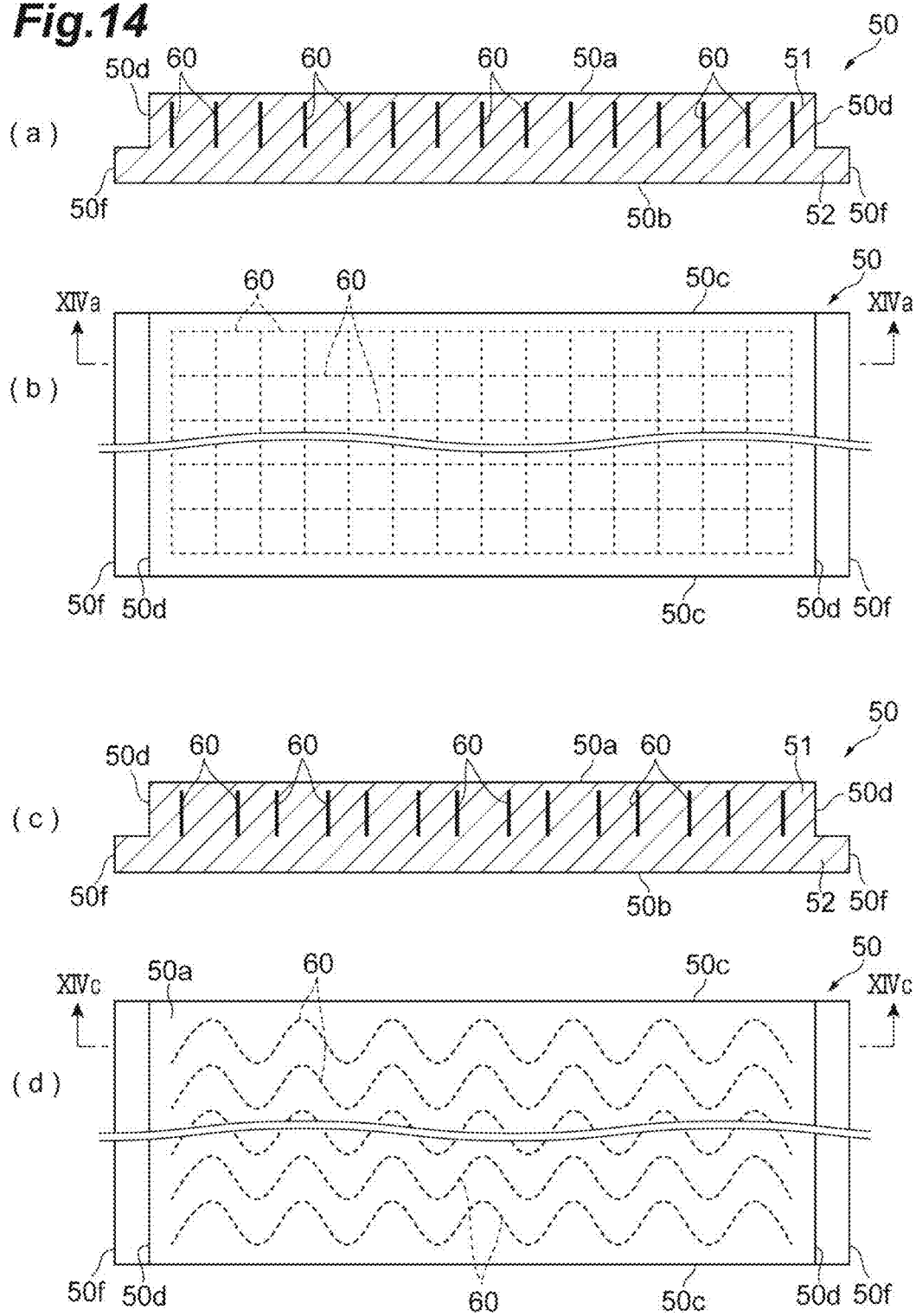
FIG. 14 is a diagram illustrating a modification example of the optical plate.

(a) of FIG. 14 is a cross-sectional view taken along line XIVa-XIVa in a plan view of (b) of FIG. 14. Further, (c) of FIG. 14 is a cross-sectional view taken along line XIVc-XIVc in a plan view of (d) of FIG. 14. As illustrated in (a) and (b) of FIG. 14, in the optical plate 50, light diffusion portions 60 may be formed in a lattice pattern along the main surface 50*a*. In this case, the light diffusion portions 60 in one direction and the light diffusion portions 60 in another direction are formed to pass between the wells 13 adjacent to each other, when viewed in the third direction.

Further, in this case, the light diffusion portions 60 in one direction and the light diffusion portions 60 in another direction may intersect each other at an angle of 90° when viewed in the third direction or may intersect each other at other angles (for example, 45°). In this case, oblique illumination (that is, illumination based on a dark field) can be preferably performed with respect to the measurement target A using light from the outside of the well 13 by forming the light diffusion portions 60 to surround the well 13 when viewed in the third direction. Further, in the optical plate 50, the present invention is not limited to the case in which the light diffusion portions 60 are formed linearly along the main surface 50*a*, and the light diffusion portions 60 may be formed in a curve shape along the main surface 50*a*, as illustrated in (c) and (d) of FIG. 14.

Further, the light diffusion portions 60 may be formed of a plurality of light diffusion layers (layers including modified regions 7) in the direction along the main surface 50*a* (that is, the first and/or second direction). That is, the respective light diffusion portions 60 may be formed of a plurality of light diffusion layers formed by converging the laser light L. More specifically, for example, in a case in which each of the light diffusion portions 60 is an aspect illustrated in FIG. 2, the light diffusion portion 60 may be formed of a first light diffusion layer including a plurality of modified regions 7 extending in the first direction and arranged in the third direction, and one (or a plurality of) second light diffusion layer formed adjacent to the first light diffusion layer and including a plurality of other modified regions 7 extending in the first direction and arranged in the third direction.

Further, for example, in a case in which the light diffusion portion 60 is an aspect illustrated in (a) and (b) of FIG. 13, the light diffusion portion 60 is formed of a first light diffusion layer including a modified region 7 having a rectangular cylindrical shape and one (or a plurality of) second light diffusion layer including another modified region 7 having a rectangular cylindrical shape that surrounds the first light diffusion layer. Further, for example, in a case in which the light diffusion portion 60 is an aspect illustrated in (c) and (d) of FIG. 13, the light diffusion portion 60 may be formed of a first light diffusion layer including a modified region 7 having a cylindrical shape and one (or a plurality of) second light diffusion layer including another concentric modified region 7 having a cylindrical shape with respect to the first light diffusion layer.

Second Embodiment

Figure 15:
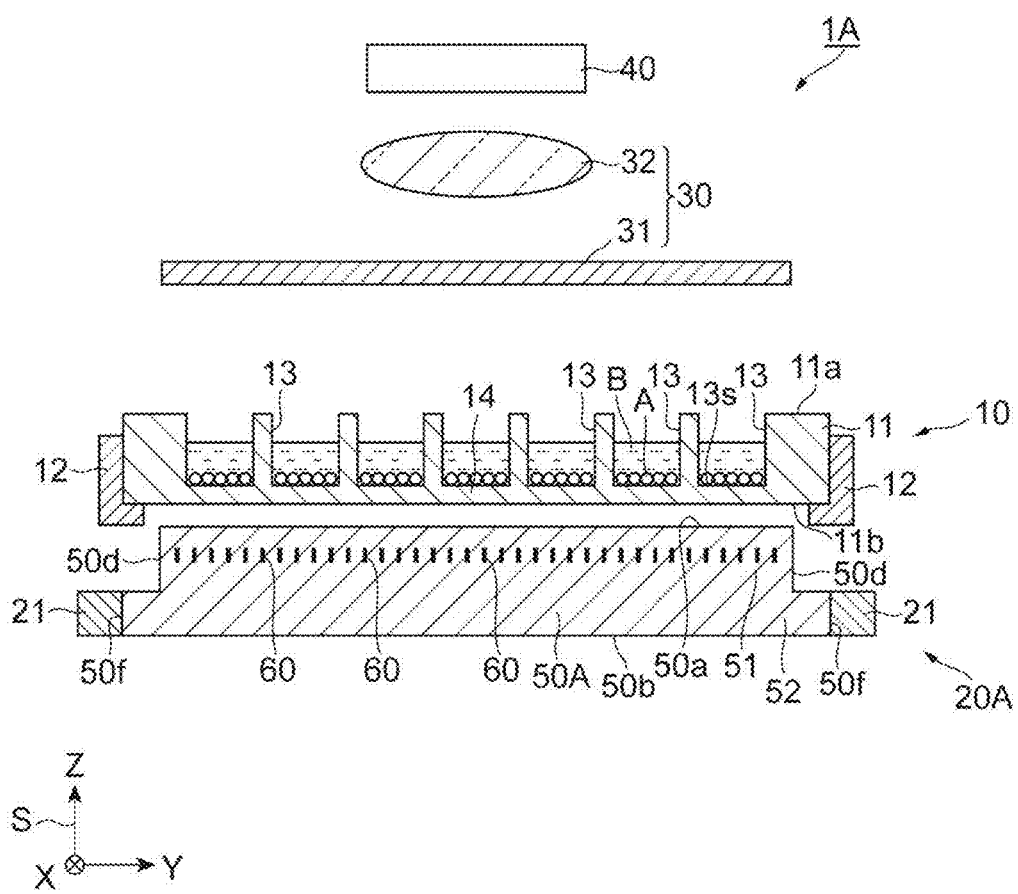
FIG. 15 is a schematic cross-sectional view illustrating a configuration of a light measurement system according to a second embodiment.

Next, a light measurement system according to a second embodiment will be described. FIG. 15 is a schematic cross-sectional view illustrating a configuration of the light measurement system according to the second embodiment. A light measurement system 1A according to the second embodiment is different from the light measurement system 1 in that the light measurement system 1A includes a light irradiation apparatus 20A in place of the light irradiation apparatus 20 and in a positional relationship of respective elements, as illustrated in FIG. 15.

The light irradiation apparatus 20A is different from the light irradiation apparatus 20 in that the light irradiation apparatus 20A includes an optical plate 50A in place of the optical plate 50. The optical plate 50A will be described in detail below. The light source 21 inputs the light from the light input surface of the optical plate 50A to the optical plate 50A. The optical system 30 transmits the measurement light (for example, fluorescence, reflected light, or scattered light) from the measurement target A irradiated with light from the light source 21 via the optical plate 50 and forms an image on the imaging device 40. The imaging device 40 images the measurement light formed by the lens 32 of the optical system 30.

In this embodiment, the light irradiation apparatus 20A is disposed on the back surface 11b side of the micro-plate 11, and the optical system 30 and the imaging device 40 are disposed in this order on the main surface 11a side of the micro-plate 11. Accordingly, the imaging device 40 receives, via the optical system 30, the measurement light emitted from the measurement target A irradiated with the light from the light irradiation apparatus 20A and output from the main surface 11a side of the micro-plate 11, and performs imaging.

Figure 16:
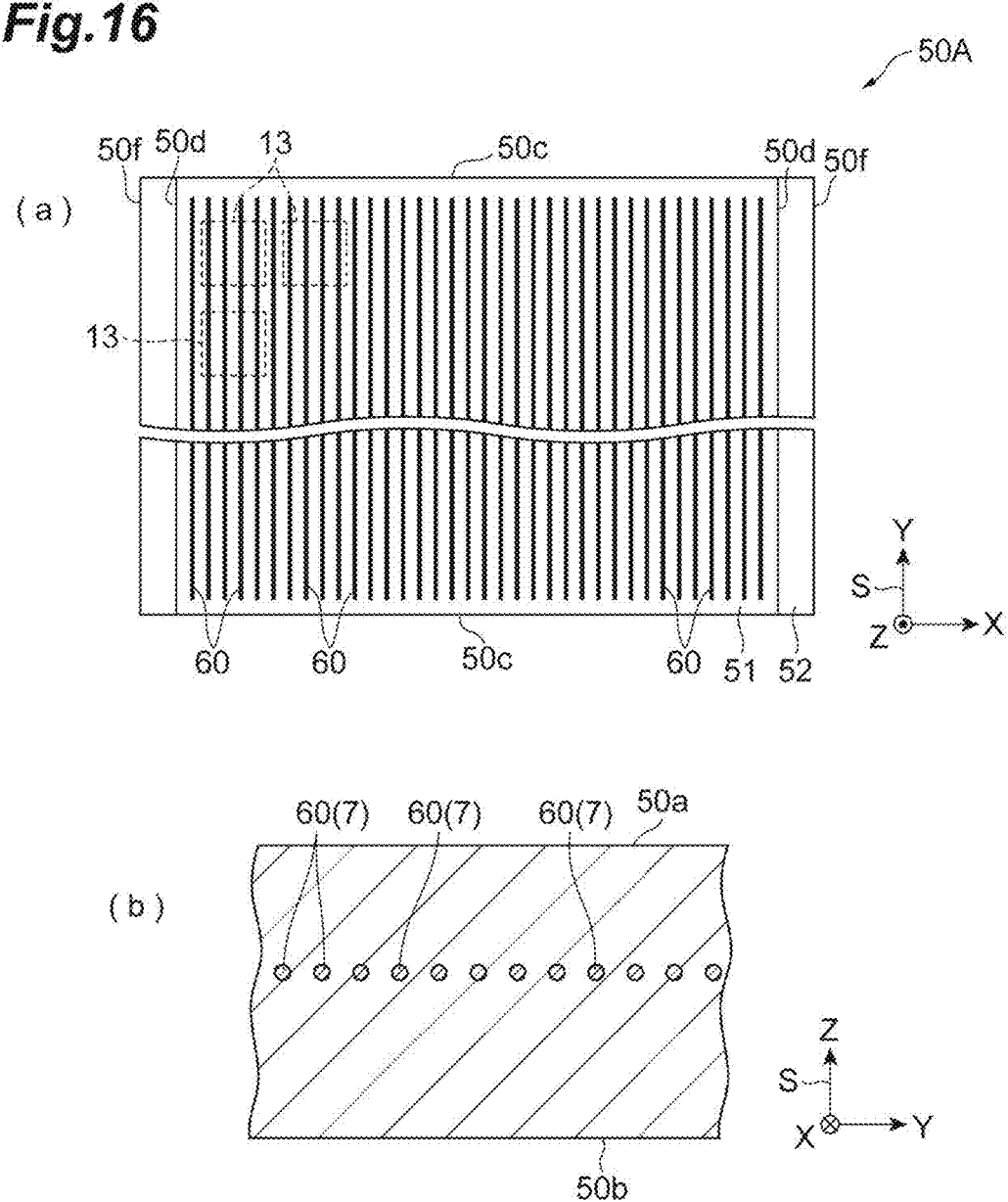
FIG. 16 is a diagram illustrating a configuration of the optical plate illustrated in FIG. 15.

FIG. 16 is a diagram illustrating a configuration of the optical plate illustrated in FIG. 15. In particular, (a) of FIG. 16 is a plan view of the optical plate 50A, and (b) of FIG. 16 is a partial cross-sectional view of the optical plate 50A. As illustrated in FIG. 16, in the optical plate 50A, an aspect of formation of the light diffusion portion 60 is different from that of the optical plate 50. More specifically, in the optical plate 50A, the light diffusion portion 60 extends between a pair of side surfaces 50c and 50c in the first direction (X-axis direction).

Further, the light diffusion portions 60 are arranged at substantially equal intervals in the second direction (Y-axis direction). The interval of the arrangement of the light diffusion portions 60 is set so that the well 13 and the plurality of lines of light diffusion portions 60 overlap when viewed in the third direction (Z-axis direction). Thus, the plurality of lines of light diffusion portions 60 are arranged directly under one well 13 when viewed in the third direction. Meanwhile, here, the light diffusion portion 60 is formed of one modified region 7 (modified spot) in the third direction. However, the light diffusion portion 60 may be formed of a plurality of modified regions 7 in the third direction, similar to the first embodiment. A method for forming the light diffusion portion 60 is the same as that in the first embodiment.

Figure 17:
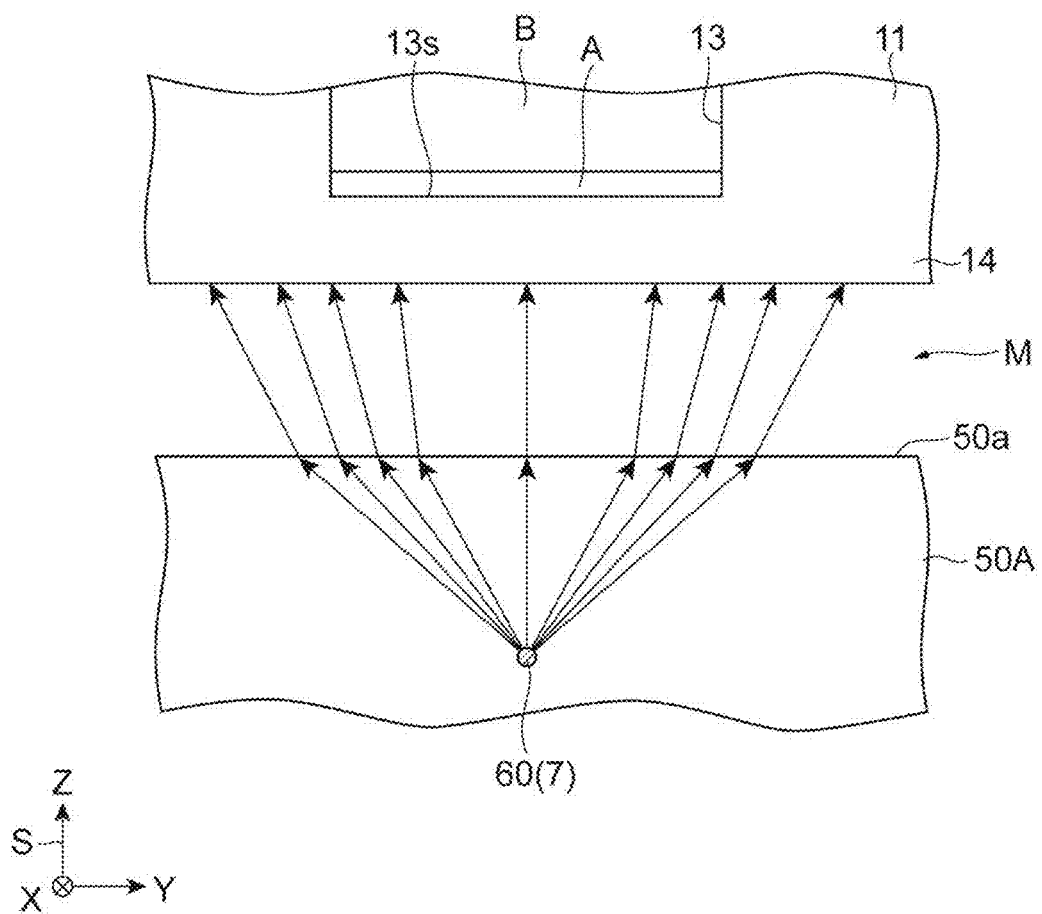
FIG. 17 is a schematic cross-sectional view illustrating a state in which light is diffused in a light diffusion portion.

FIG. 17 is a schematic cross-sectional view illustrating a state in which light is diffused in the light diffusion portion. In the first embodiment, the intermediate layer M between the micro-plate 11 and the optical plate 50 is formed of a material (for example, air) with a refractive index smaller than the refractive index of the optical plate 50. In this embodiment, a case in which the intermediate layer M between the micro-plate 11 and the optical plate 50A is formed of a material with a refractive index higher than the refractive index of the material of the optical plate 50 is assumed. An example of the intermediate layer M in this case includes a layer formed by disposing a resin such as silicone, oil, water, and the like between the main surface 50a of the optical plate 50A and the back surface 11b of the micro-plate 11.

Accordingly, the light diffused in the light diffusion portion 60 is refracted at a small degree of diffusion between the main surface 50a and the intermediate layer M (that is, refracted at a small angle with respect to the depth direction of the well 13) and output from the main surface 50a. As described above, the light diffusion portion 60 is also disposed directly under the well 13. Therefore, the measurement target A is sufficiently illuminated by light with relatively small spread.

Figure 18:
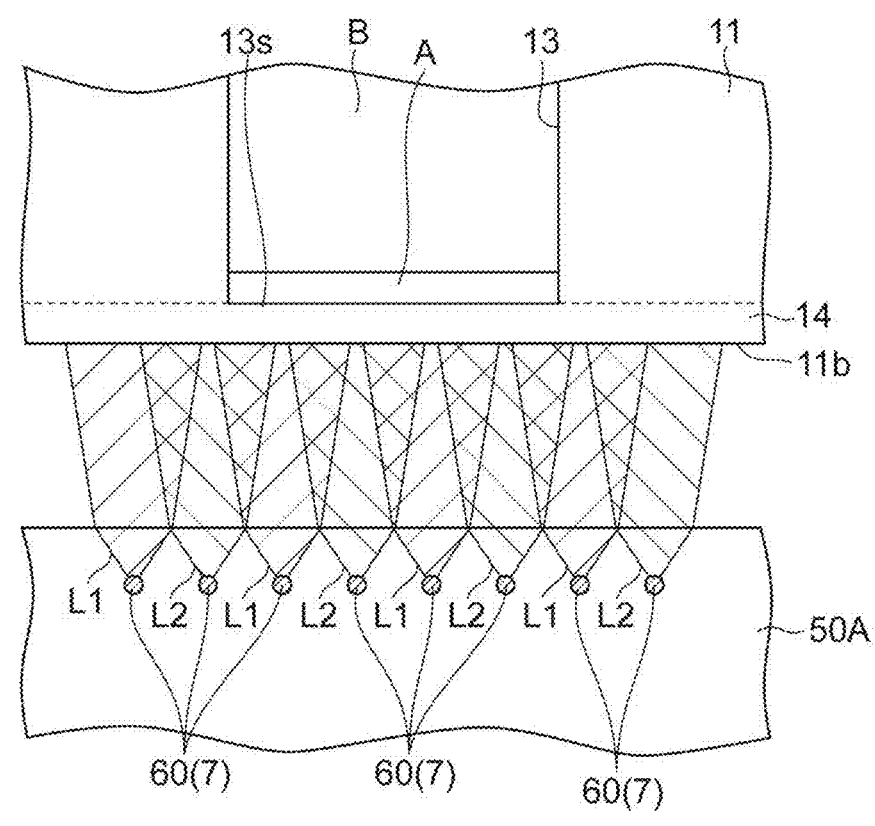
FIG. 18 is a schematic cross-sectional view illustrating a state in which a measurement target is irradiated with light from a plurality of light diffusion portions disposed directly under wells.

FIG. 18 is a schematic cross-sectional view illustrating a state in which the measurement target is irradiated with light from a plurality of light diffusion portions disposed directly under the wells. As illustrated in FIG. 18, here, the lights L1 and L2 diffused in the light diffusion portions 60 adjacent to each other are alternately superposed and radiated to the measurement target A held in the well 13. In other words, the measurement target A can be illuminated by the lights L1 and L2 from directly under the well 13 when viewed in the third direction. Therefore, transmission illumination (that is, illumination based on a bright field) can be preferably performed with respect to the measurement target A.

As described above, in the light measurement system 1A according to this embodiment, it is possible to perform irradiation with light according to desired irradiation conditions, similar to the light measurement system 1 according to the first embodiment. In particular, in the light measurement system 1A, the measurement target A held in the well 13 is irradiated with the light diffused in the plurality of light diffusion portions 60 disposed directly under the well 13 at a relatively small angle with respect to the depth direction (third direction) of the well 13. Accordingly, it is possible to preferably perform illumination based on a bright field.

Various modification examples of the optical plate 50 according to the first embodiment are also effective in the optical plate 50A according to this embodiment. That is, in a range in which a plurality of light diffusion portions 60 are disposed for one well 13 when viewed in the third direction, the light diffusion portions 60 may be formed in a rectangular cylindrical shape or a cylindrical shape or the light diffusion portions 60 may be formed in a grid shape or a curve shape along the main surface 50a. Alternatively, a forming position or a length of the light diffusion portion 60 in the third direction may be appropriately set. Further, a reflective portion 80 may be further included.

Third Embodiment

Next, a light measurement system according to a third embodiment will be described. FIG. 19 is a diagram illustrating a configuration of a light measurement system according to a third embodiment. In particular, (a) of FIG. 19 is a schematic cross-sectional view taken along line XIXa-XIXa in a plan view of (b) of FIG. 19, and (c) of FIG. 19 is a side view. As illustrated in FIG. 19, a light measurement system 1B according to the third embodiment is different from the light measurement system 1 in that the light measurement system 1B includes a light irradiation apparatus 20B in place of the light irradiation apparatus 20. In FIG. 19, the optical system 30 and the imaging device 40 are omitted.

The light irradiation apparatus 20B is different from the light irradiation apparatus 20 in that the light irradiation apparatus 20B includes an optical plate 50B in place of the optical plate 50. The optical plate 50B includes a pair of reflective portions 90. The reflective portion 90 extends in a third direction intersecting the main surface 50a that is a light output surface of the optical plate 50B. The reflective portion 90 is provided on the side surface 50c intersecting the side surface 50f that is a light input surface in the optical plate 50B. The reflective portion 90 exhibits the same effects as those of the first reflective region 81 of the reflective portion 80 described above.

Further, a mask 97 is provided on the main surface 50a of the optical plate 50 B. The mask 97 has a rectangular annular shape when viewed in the third direction, and is provided in an outer periphery of the main surface 50a. Thus, in the main surface 50a, only a portion other than an outer peripheral portion thereof is exposed from an opening 97h of the mask 97. A dimension of the opening 97h of the mask 97 is defined so that an entire region in which the well 13 of the micro-plate 11 is formed is included in an exposed portion of the main surface 50a from the opening 97h when viewed in the third direction.

Further, the optical plate 50B includes a reflective portion 95 provided upright on the mask 97. The reflective portion 95 extends in the third direction intersecting the main surface 50a that is a light output surface of the optical plate 50B. The reflective portion 95 has a rectangular annular shape to be along an outer edge of the opening 97h of the mask 97 when viewed in the third direction. The reflective portion 95 has the same effects as those of the second reflective region 82 of the reflective portion 80 described above.

Here, the optical plate 50B includes a plurality of dot-like light diffusion portions 60 arranged in a two-dimensional array along the main surface 50a when viewed in the third direction, as illustrated in FIGS. 19 and 20. Each of the light diffusion portions 60 includes a single modified region 7 (modified spot) in the first and second directions. On the other hand, each of the light diffusion portion 60 includes a plurality (here, two) modified regions 7 (modified spots) in the third direction. A method of forming the light diffusion portion 60 is the same as in the first embodiment.

An arrangement of the light diffusion portions 60 when viewed in the third direction is defined as follows. That is, a dimension or an arrangement of the light diffusion portions 60 is defined so that a ratio of an area of the light diffusion portion 60 to an area of a single pixel PA of the imaging device (imaging element) 40 is less than 10% when viewed in the third direction, as illustrated in (b) of FIG. 20. For example, if one light diffusion portion 60 of about 0.02 mm×0.02 mm is disposed in the pixel PA when an area of the pixel PA of the imaging device 40 is about 0.25 mm×0.25 mm, an area ratio is about 0.64%. Thus, if a processing area of the light diffusion portion 60 is less than a field of view size, the light diffusion portion 60 is not manifested as an image and uneven imaging can be avoided at the time of imaging of the imaging device 40.

Thus, in the light measurement system 1B according to this embodiment, it is possible to performs irradiation of the light according to desired irradiation conditions, similar to the light measurement system 1 according to the first embodiment. Further, it is possible to avoid uneven imaging as described above.

The optical plate, the light irradiation apparatus, and the light measurement system according to an aspect of the present invention have been described in the above-described embodiment. Thus, the optical plate, the light irradiation apparatus, and the light measurement system according to an aspect of the present invention are not limited to those described above.

For example, the case in which the measurement target A is held in the well 13 of the micro-plate 11 has been described in the first to third embodiments. However, the optical plate (that is, the light irradiation apparatus, the light measurement system, the light irradiation method, and the light measurement method) according to an aspect of the present invention is applicable to a case in which the measurement target A is held in another holding member such as a petri dish or a glass slide.

Figure 21:
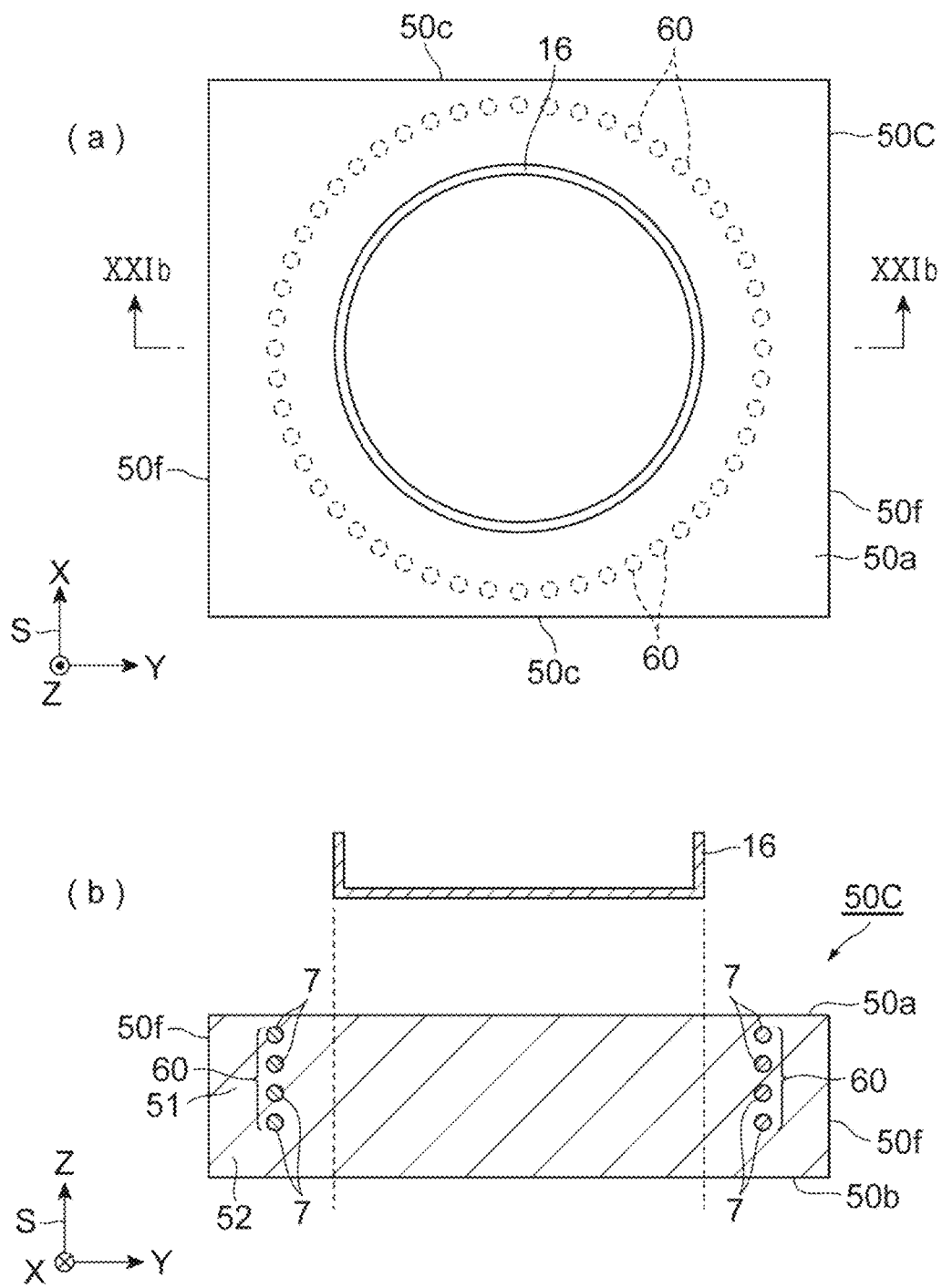
FIG. 21 is a diagram illustrating an example in a case in which a measurement target is held in a petri dish.

FIG. 21 is a diagram illustrating an example in which a measurement target is held in a petri dish. (b) of FIG. 21 is a cross-sectional view taken along line XXIb-XXIb in (a) of FIG. 21. As illustrated in FIG. 21, here, the measurement target A is held in a petri dish (holding member) 16, and an optical plate 50C is used accordingly. A plurality of light diffusion portions 60 arranged in an annular shape are formed in the optical plate 50C to surround the petri dish 16 when viewed in the third direction. That is, the light diffusion portions 60 are not formed directly under the petri dish 16. Further, the respective light diffusion portions 60 include a plurality of modified regions 7 (modified spots) in the third direction. That is, the light diffusion portion 60 extends in the third direction.

In this case, irradiation with light according to desired irradiation conditions can be performed, similar to the above embodiment. Further, since the measurement target A can be illuminated by light from the outside of the petri dish 16 when viewed in the third direction, oblique illumination (that is, illumination based on a dark field) can be preferably performed with respect to the measurement target A.

FIG. 22 is a diagram illustrating another example in which a measurement target is held in a petri dish. (b) of FIG. 22 is a cross-sectional view taken along line XXIb-XXIb in (a) of FIG. 22. As illustrated in FIG. 22, here, the measurement target A is held in a petri dish (holding member) 16, and an optical plate 50D is used accordingly. A plurality of light diffusion portions 60 are formed along the main surface 50a in the optical plate 50D. More specifically, the plurality of light diffusion portions 60 are formed in the optical plate 50D to overlap the petri dish 16 when viewed in the third direction. Accordingly, the plurality of light diffusion portions 60 are disposed directly under the petri dish 16 when viewed in the third direction. Each light diffusion portion 60 includes a single modified region 7 (modified spot) in the third direction.

In this case, irradiation with light according to desired irradiation conditions can be performed, similar to the above embodiment. Further, since the measurement target A can be illuminated by light from directly under the Petri dish 16 when viewed in the third direction, transmission illumination (that is, illumination based on a bright field) can be preferably performed with respect to the measurement target A.

Figure 23:
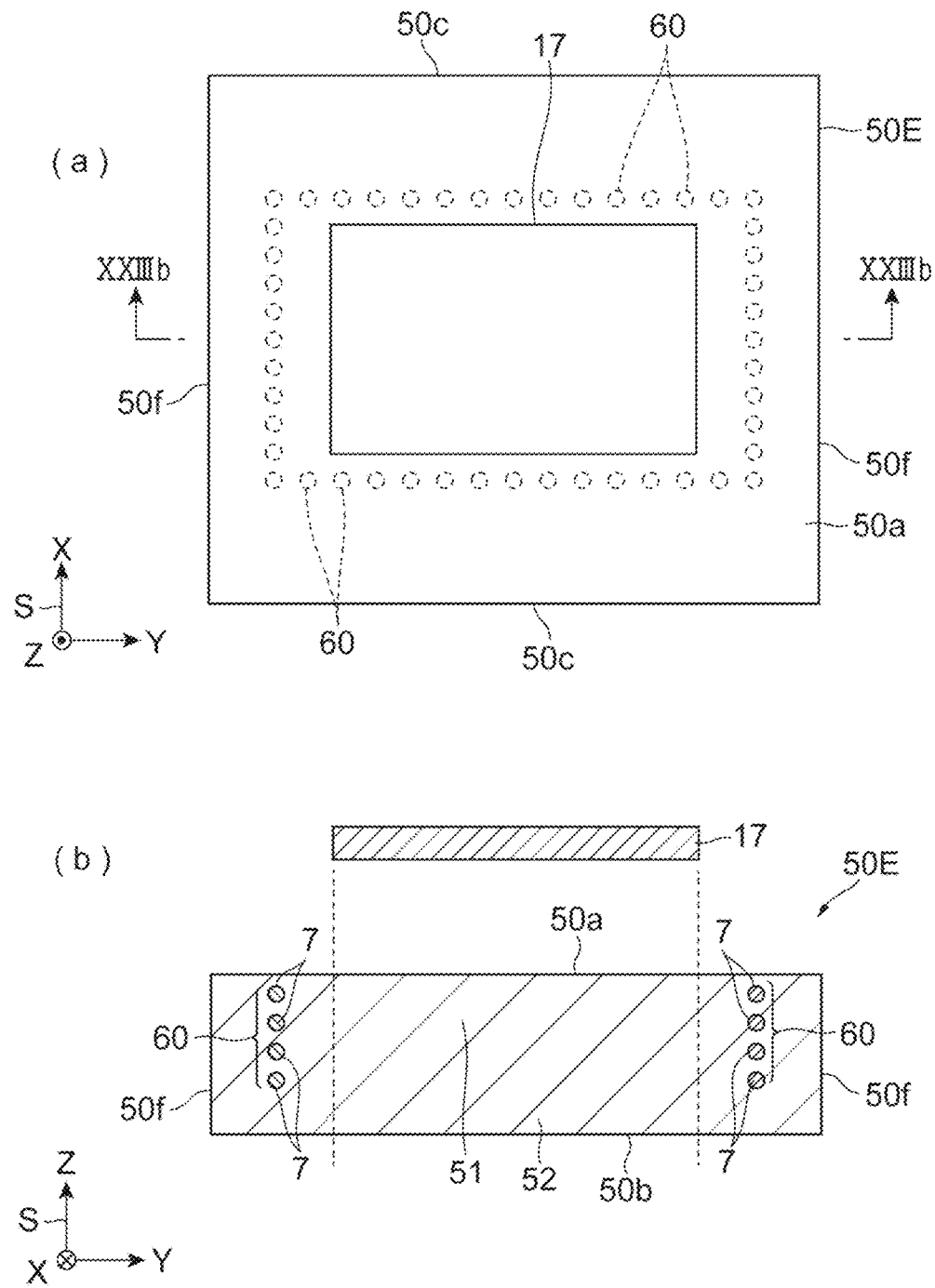
FIG. 23 is a diagram illustrating an example in a case in which a measurement target is held in a glass slide.

FIG. 23 is a diagram illustrating an example in which a measurement target is held in a glass slide. (b) of FIG. 23 is a cross-sectional view taken along line XXIIIb-XXIIIb in (a) of FIG. 23. As illustrated in FIG. 23, here, the measurement target A is held in a glass slide having a rectangular plate shape (holding member) 17, and an optical plate 50E is used accordingly. A plurality of light diffusion portions 60 arranged in a rectangular annular shape are formed in the optical plate 50E to surround the glass slide 17 when viewed in the third direction. That is, the light diffusion portions 60 are not formed directly under the glass slide 17. Further, the respective light diffusion portions 60 include a plurality of modified regions 7 (modified spots) in the third direction. That is, the light diffusion portion 60 extends in the third direction.

In this case, irradiation with light according to desired irradiation conditions can be performed, similar to the above embodiment. Further, since the measurement target A can be illuminated by light from the outside of the glass slide 17 when viewed in the third direction, oblique illumination (that is, illumination based on a dark field) can be preferably performed with respect to the measurement target A.

FIG. 24 is a diagram illustrating another example in which a measurement target is held in a glass slide. (b) of FIG. 24 is a cross-sectional view taken along line XXIVb-XXIVb in (a) of FIG. 24. As illustrated in FIG. 24, here, the measurement target A is held in a glass slide (holding member) 17, and an optical plate 50F is used accordingly. A plurality of light diffusion portions 60 are formed along the main surface 50a in the optical plate 50F. More specifically, the plurality of light diffusion portions 60 are formed in the optical plate 50F to overlap the glass slide 17 when viewed in the third direction. Accordingly, the plurality of light diffusion portions 60 are disposed directly under the glass slide 17 when viewed in the third direction. Each light diffusion portion 60 includes a single modified region 7 (modified spot) in the third direction.

In this case, irradiation with light according to desired irradiation conditions can be performed, similar to the above embodiment. Further, since the measurement target A can be illuminated by light from directly under the glass slide 17 when viewed in the third direction, transmission illumination (that is, illumination based on a bright field) can be preferably performed with respect to the measurement target A.

As described above, various aspects of the formation of the light diffusion portions in the optical plate can be assumed. The aspects of the formation of the light diffusion portions in the optical plate are determined, for example, as follows. That is, first, a specification of the optical system is set. More specifically, an excitation wavelength from the light source, and a distance and the number of intermediate layers are set. Here, the intermediate layer may be, for example, at least one of a layer (for example, the intermediate layer M) between the main surface of the optical plate and the back surface of the holding member such as the micro-plate, and a layer (for example, a bottom portion 14 of the micro-plate 11) from the back surface of the holding member such as the micro-plate to a mounting surface for the measurement target (for example, the bottom surface 13s of the well 13) in the holding member. Further, the length of the intermediate layer is a dimension in the third direction of the layer.

Subsequently, after a specification of the optical system is set, a specification of an illumination symmetry is set. More specifically, a setting of a shape of the illumination target (the holding member and the measurement target) (that is, a setting of the irradiation conditions), a setting of a specification (for example, light distribution characteristics, a bright field or a dark field, and an acceptable degree of uneven irradiation) of the input light, and a setting of a required amount of light are performed.

Thereafter, a refractive index of the optical plate, a refractive index of the intermediate layer, and a shape of the optical plate are set. By this setting, an aspect of the light diffusion portion formed in the optical plate is determined. That is, a position or a pattern in the first to third directions of the light diffusion portion formed in the optical plate is determined. Accordingly, an aspect of the light diffusion portion in the optical plate is not limited to the specific examples described above and may be appropriately set according to various conditions.

Further, an illumination target (for example, the measurement target A) is not limited to cells or a tissue including cells, and may be an industrial product such as a semiconductor device or a film. Further, the light measurement system of the above embodiment may be a microscope system such as an optical microscope or a digital slide scanner. In this case, an objective lens may be further included, if necessary.

INDUSTRIAL APPLICABILITY

According to an aspect of the present invention, it is possible to provide the optical plate, the light irradiation apparatus, the light measurement system, the light irradiation method, and the light measurement method capable of allowing irradiation with light according to desired irradiation conditions.

REFERENCE SIGNS LIST

1: light measurement system
11: micro-plate (holding member)
16: petri dish (holding member)
17: glass slide (holding member)
20, 20A, 20B: light irradiation apparatus
21: light source
40: imaging device (light detector)
50, 50A, 50B, 50C, 50D, 50E, 50F: optical plate
50a: main surface (light output surface)
50b: back surface (light output surface)
50d, 50f: side surface (light input surface)
51: first portion
52: second portion
60, 61, 62: light diffusion portion
80, 90, 95: reflective portion
A: measurement target (target)
L1, L2, L3, L4: light
L: laser light

The invention claimed is:
1. A light measurement system, comprising:
a light irradiation apparatus, comprising:
an optical plate for irradiating a target with light, comprising:
a light input surface configured to input the light;
a light diffusion portion formed at least inside the optical plate by converging laser light, and configured to diffuse the light input from the light input surface,
a light output surface configured to output the light diffused in the light diffusion portion; and
a back surface opposite to the light output surface, wherein the light input surface is a surface between the light output surface and the back surface; and
a light source configured to output the light to be input to the light input surface;

a holder configured to hold the target; and a light detector configured to detect measurement light from the target irradiated with the light output from the light output surface.

2. The light measurement system according to claim 1, the optical plate further comprising:

a light guide portion configured to guide the light between the light input surface and a surface facing the light input surface.

3. The light measurement system according to claim 2, the optical plate further comprising:

a first portion in which the light diffusion portion is formed, and a second portion formed integrally with the first portion, wherein the light guide portion is formed in the second portion.

4. The light measurement system according to claim 2, wherein the optical plate is formed by coupling a first portion in which the light diffusion portion is formed to a second portion formed separately from the first portion, and the light guide portion is formed in the second portion.

5. The light measurement system according to claim 1, wherein the light diffusion portion is formed over at least a portion between the light output surface and the back surface.

6. The light measurement system according to claim 1, wherein the light diffusion portion is formed of a plurality of light diffusion layers formed by converging the laser light.

7. The light measurement system according to claim 1, further comprising:

a reflective portion extending in a direction intersecting the light output surface, and configured to reflect the light.

8. The light measurement system according to claim 1, wherein the light detector is configured to detect the measurement light transmitted through the optical plate and output from the back surface.

9. A light measurement method for irradiating a target with light using an optical plate including a light output surface configured to output the light, a back surface opposite to the light output surface, a light input surface being a surface between the light output surface and the back surface, and configured to input the light, and a light diffusion portion formed by converging laser light, and detecting measurement light from the target irradiated with the light, the light measurement method comprising:

inputting the light to the light input surface;

diffusing the input light in the light diffusion portion;

outputting the diffused light from the light output surface;

irradiating the target with the output light; and detecting the measurement light from the target transmitted through the light output surface and the back surface.

* * * * *